US006171779B1

(12) United States Patent
Chada et al.

(10) Patent No.: US 6,171,779 B1
(45) Date of Patent: *Jan. 9, 2001

(54) HMGI PROTEINS IN CANCER

(75) Inventors: Kiran K. Chada, North Brunswick; Hena Ashar, Edison; Alex Tkachenko, New Brunswick; Xianjin Zhou, Piscataway, all of NJ (US)

(73) Assignee: University of Medicine & Dentistry of New Jersey, Newark, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/679,529

(22) Filed: Jul. 12, 1996

(51) Int. Cl.[7] .............................. C12Q 1/00; C12Q 1/68; G01N 33/53; G01N 33/574
(52) U.S. Cl. ................................... 435/4; 435/6; 435/7.1; 435/7.2; 435/7.23
(58) Field of Search ............................ 435/7.1, 4; 514/12

(56) References Cited

PUBLICATIONS

Manfioletti et al, (Nucleic Acid Res, 1991, 19: 6793–6797).
Ashar et al (Cell, 1995, 82.–57–65).
Schoenmakers et al, (Nature Gen., 1995, 10:436–444).
Cooper (Corr. Opin. Genet. Dev, 1996, 6:71–75).
Schoenberg et al (Am J. Human Gen;1995, 57(4 Supp 10, A4).

*Primary Examiner*—Susan Ungar
(74) *Attorney, Agent, or Firm*—Richard R. Muccino

(57) ABSTRACT

The present invention pertains to a method for detecting HMGI-C or HMGI(Y) as a diagnostic marker for benign or malignant tumors using a probe for a sample from a patient that recognizes HMGI-C or HMGI(Y). The method comprises the steps of (a) contacting HMGI-C or HMGI(Y) from a sample from a patient with a probe which binds to HMGI-C or HMGI(Y); and (b) analyzing for HMGI-C or HMGI(Y) by detecting levels of the probe bound to the HMGI-C or HMGI(Y). The presence of HMGI-C or HMGI (Y) in the sample is positive for a benign or malignant tumor. The present invention also pertains to a method for detecting antibodies to HMGI-C or HMGI(Y) as a diagnostic marker for benign or malignant tumors. The present invention further pertains to a method for treating benign and malignant tumors in a patient by blocking the biological activity of HMGI-C or HMGI(Y). The present invention also pertains to a method for treating obesity in a patient by blocking the biological activity of HMGI-C or HMGI(Y).

9 Claims, 11 Drawing Sheets

Figure 1
A.
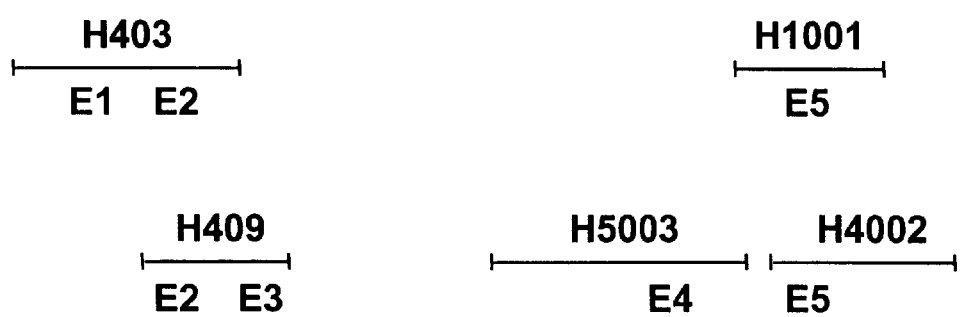
B.
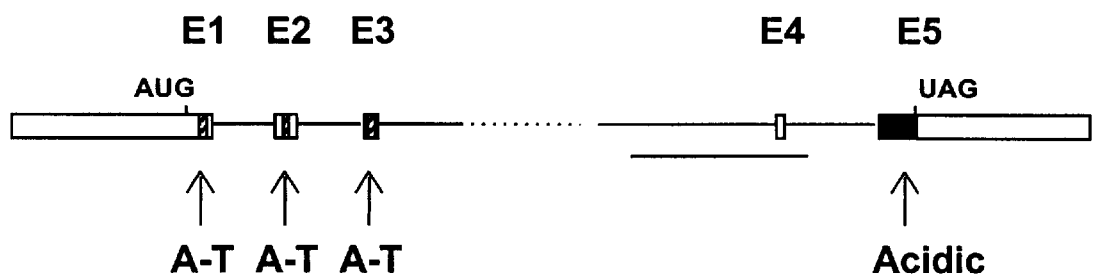

| | | | | |
|---|---|---|---|---|
| Chr. 3: 1 | QCNVCSKPI.[x9]..KAYHPHCFTCVMCHRSL.[x11].LIHCIEDF |
| Zyxin: 2 | KCSVCKQTI.[x9]..NSYHPQCFTCVMCHTPL.[x11].QPHCVDDY |
| Ap: 1 | DCSGCGRQI.[x10].KRWHASCLKCYACRQPL.[x11].NIYCKNDY |
| Lh2: 1 | LCAGCGGKI.[x10].KQWHMRCLKCCECKLNL.[x11].SIYCKEDY |
| Lin11: 1 | ECAACAQPI.[x10].KCWHQSCLRCCDCRAPM.[x9]..LILCKTDF |
| RBTN-1: 1 | GCAGCNRKI.[x10].KYWHEDCLKCACCDCRL.[x12].LILCRRDY |

| | |
|---|---|
| Chr. 3: 2 | RCSVCKEPI.[x15].SRFHVHCYRCEDCGGLL.[x13].HILCKTCN |
| Zyxin: 3 | RCSVCSEPI.[x16].KNFHMKCYKCEDCGRPL.[x14].HVLCMKCH |
| Ap: 2 | RCSRCLASI.[x11].LVFHVNCFCCTVCH.PL.[x11].LIYCRTHY |
| Lh2: 2 | RCARCHLGI.[x11].LVYHNLCFTCTTCN.ML.[x11].LVYCRLHF |
| Lin11: 2 | RCAGCDGKL.[x11].KVFHIRCFQCSVCQRLL.[x12].RFVCQSDF |
| RBTN-1: 2 | NCAACSKLI.[x11].NVYHLDCFACQLCNQRF.[x12].IL.CQMDY |

Consensus  CxxC   x16-21   HxxCxxCxxC   x16-21   CxxH/D (with C above)

B.

<u>Chr. 15</u>   EEEEH LNTERSSAGGGWRGVQPLGS PTPGEDHRPIPSPASGFPSI

Figure 10
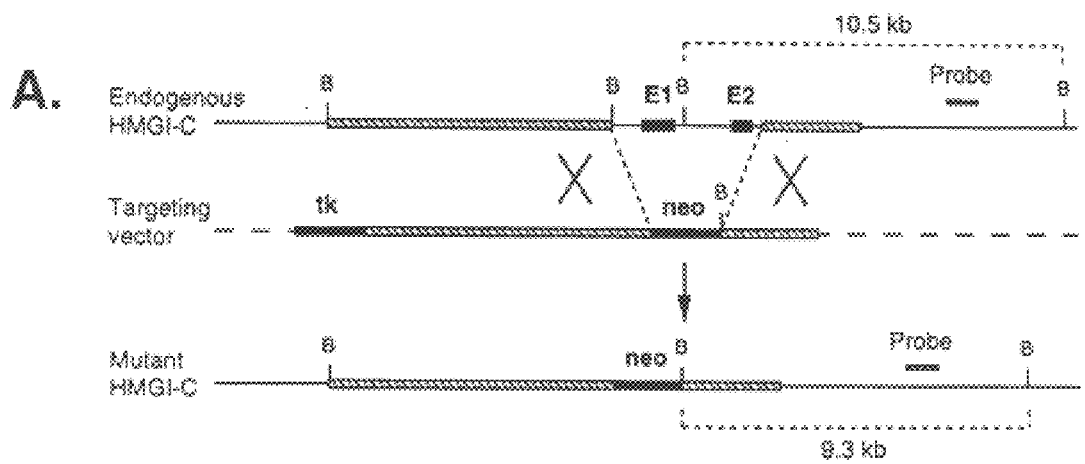
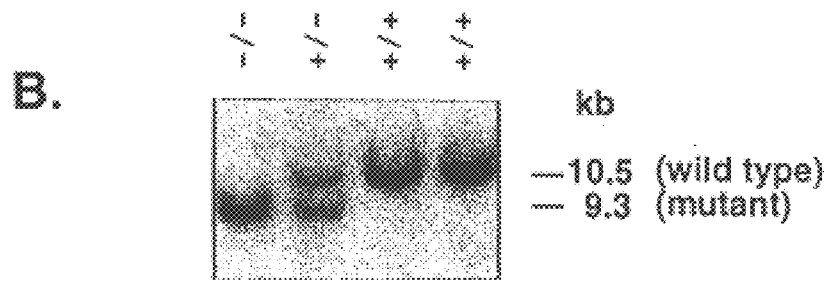
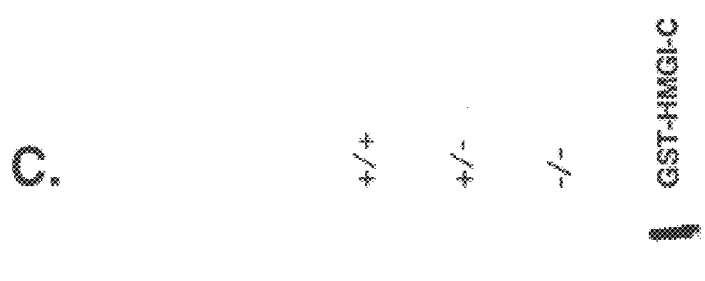

Figure 11
A.
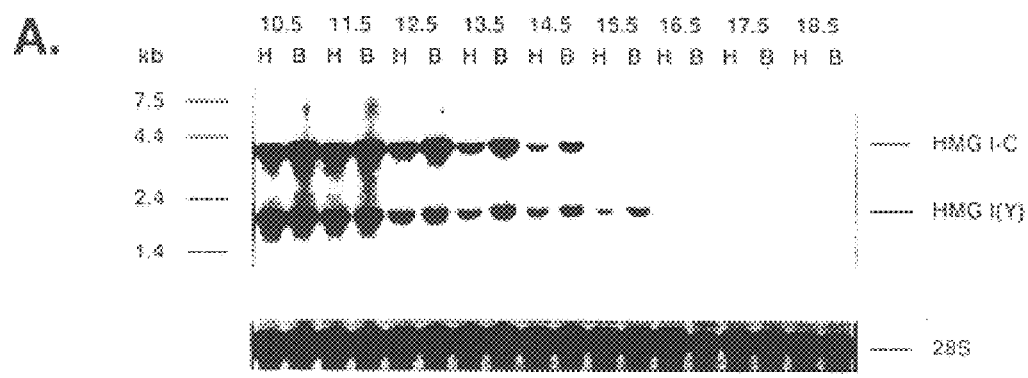
B.
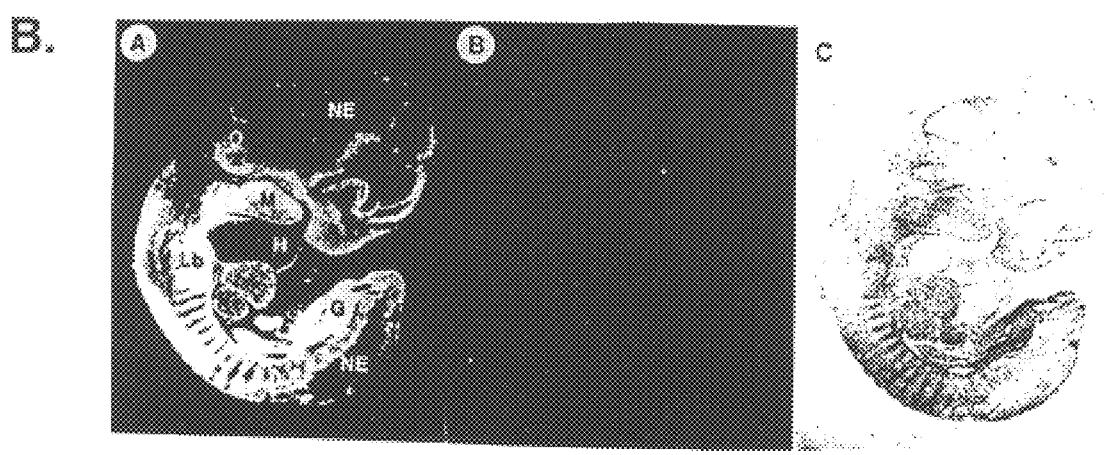
C.
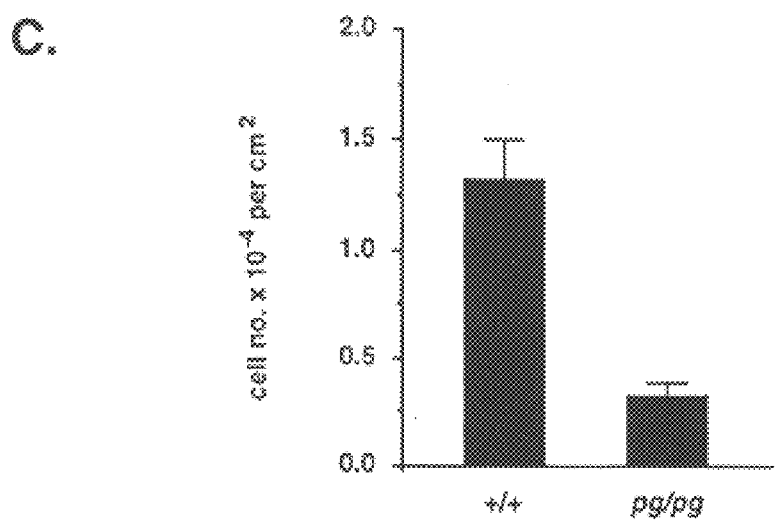

HMGI PROTEINS IN CANCER

STATEMENT OF RIGHTS TO INVENTIONS MADE UNDER FEDERALLY-SPONSORED RESEARCH AND DEVELOPMENT

Part of the work performed during development of this invention utilized United States Government funds. The United States Government has certain rights in this invention: NIH grant no. GM38731, HD30498, and 1K11CA01498.

BACKGROUND OF THE INVENTION

1. Field of the Invention

The present invention pertains to a method for detecting HMGI-C or HMGI(Y) as a diagnostic marker for benign or malignant tumors using a probe for a sample from a patient that recognizes HMGI-C or HMGI(Y). The method comprises the steps of (a) contacting HMGI-C or HMGI(Y) from a sample from a patient with a probe which binds to HMGI-C or HMGI(Y); and (b) analyzing for HMGI-C or HMGI(Y) by detecting levels of the probe bound to the HMGI-C or HMGI(Y). The presence of HMGI-C or HMGI(Y) in the sample is positive for a benign or malignant tumor. The present invention also pertains to a method for detecting antibodies to HMGI-C or HMGI(Y) as a diagnostic marker for benign or malignant tumors. The present invention further pertains to a method for treating benign and malignant tumors in a patient by blocking the biological activity of HMGI-C or HMGI(Y). The present invention also pertains to a method for treating obesity in a patient by blocking the biological activity of HMGI-C or HMGI(Y).

2. Description of the Background

The disclosures referred to herein to illustrate the background of the invention and to provide additional detail with respect to its practice are incorporated herein by reference and, for convenience, are referenced in the following text and respectively grouped in the appended bibliography.

HMGI Proteins in Adipogenesis and Mesenchyme Differentiation Understanding various genes and pathways underlying development of multicellular organisms provide insights into the molecular basis of the highly regulated processes of cellular proliferation and differentiation. In turn, genetic aberrations in control of cell growth lead to a variety of developmental abnormalities and, most prominently, cancer (Aaronson, 1991). To pursue identification of genes involved in these fundamental biological processes, the viable pygmy mutation (MacArthur, 1944) was investigated because it gives rise to mice of small stature due to a disruption in overall growth and development of the mouse. An insertional transgenic mutant facilitated cloning of the locus (Xiang et al., 1990) and subsequently it was shown that expression of the HMGI-C gene was abrogated in three pygmy alleles (unpublished results).

HMGI-C belongs to the HMG (high mobility group) family of DNA-binding proteins which are abundant, heterogeneous, non-histone components of chromatin (Grosschedl et al., 1994). HMG proteins are divided into three distinct families, the HMG box-containing HMG1/2, the active chromatin associated HMG14/17 and the HMGI proteins (Grosschedl et al., 1994). At present, the last family consists of two genes, HMGI(Y) (Johnson et al., 1988; Friedmann et al., 1993) which produces two proteins via alternative splicing (Johnson et al., 1989) and HMGI-C (Manfioletti et al., 1991; Patel et al., 1994). A prominent feature of HMGI proteins is the presence of DNA-binding domains which bind to the narrow minor groove of A-T rich DNA (Reeves and Nissen, 1990) and are therefore referred to as A-T hooks. Recently, valuable insights have been gained into their mechanism and role in transcription (Thanos and Maniatis, 1992; Du et al., 1993). The HMGI proteins have no transcriptional activity per se (Wolffe, 1994), but through protein-protein and protein-DNA interactions organize the framework of the nucleoprotein-DNA transcriptional complex. This framework is attained by their ability to change the conformation of DNA and these proteins are therefore termed architectural factors (Wolffe, 1994). In the well-studied case of HMGI(Y) and the interferon B promoter, HMGI(Y) stimulates binding of NF-KB and ATF-2 to appropriate sequences and alters the DNA structure which allows the two factors to interact with each other and presumably with the basal transcription machinery (Thanos and Maniatis, 1992; Du et al., 1993).

A number of studies have revealed an association between increased expression levels of HMGI proteins and transformation (Giancotti et al., 1987, 1989, 1993). For example, in chemically, virally or spontaneously derived tumors, appreciable expression of HMGI-C was found in contrast to no detectable expression in normal tissues or untransformed cells (Giancotti et al., 1989). A recent study has demonstrated a more direct role for HMGI-C in transformation (Berlingieri et al., 1995). Cells infected with oncogenic retroviruses failed to exhibit various phenotypic markers of transformation if HMGI-C protein synthesis was specifically inhibited.

DNA probes adjacent to HMGI-C were mapped to the distal portion of mouse chromosome 10 in a region syntenic to the long arm of human chromosome 12 including and distal to band q13 (Justice et al., 1990). This genomic region is under intensive investigation because it is the location of consistent rearrangements in a number of neoplasms, mainly of mesenchymal origin (Schoenberg Fejzo et al., 1995). Lipomas, tumors mainly composed of mature fat cells, are one of the most common mesenchymal neoplasms that occur in humans (Sreekantaiah et al., 1991). Approximately 50% of lipomas are characterized by cytogenetic rearrangements and the predominant alteration is a presumably balanced translocation involving 12q14–15 with a large variety of chromosomal partners including 1,2,3,4,5,6,7,10,11,13,15, 17,21, and X (Sreekantaiah et al., 1991; Fletcher et al., 1993). This variability in reciprocal translocations along with duplications, inversions, and deletions of 12q14–15 in these tumors, strongly indicates a primary role of a gene on chromosome 12 in lipomas. Furthermore, this gene may play a key role in normal differentiation of primitive mesenchyme as not only lipomas, but also uterine leiomyomas (smooth muscle tumors), lipoleiomyomas (smooth muscle and adipose components), and pulmonary chondroid hamartomas (primitive mesenchyme, smooth muscle, adipose, and mature cartilage components) are all clonal proliferations that are characterized by rearrangements of 12q14–15 (Schoenberg Fejzo et al., 1995).

Interestingly, breakpoints in a lipoma, a pulmonary chondroid hamartoma and uterine leiomyomata have been shown to map within a single YAC (Schoenberg Fejzo et al., 1995).

HMGI Proteins in Mammalian Growth and Development

The first step in the molecular definition of the pygmy mutation was made possible by the isolation of a transgenic insertional mouse mutant at the locus, $pg^{TgN40ACha}$ (Xiang et al., 1990). A 0.5 kb ApaI—ApaI single copy genomic sequence 2 kb from the site of transgene insertion was identified (Xiang et al., 1990) and used to initiate a bi-directional chromosome walk on normal mouse genomic DNA. The analysis of seven overlapping clones spanning 91kb delineated a 56 kb common deletion between two informative mutants, pg and pg$^{TgN40Cha}$ (FIG. 8a).

The common area of disruption was investigated further for candidate transcription units. The technique of exon amplification (Buckler et al., 1991) was employed to identify putative exons and clones 803 and 5B, in the same orientation, produced spliced products (FIG. 8b). Their sequence was determined (Ausubel et al., 1988) and a comparison to DNA sequence databases (GenBank and EMBL) revealed 100% homology to a previously identified gene, HMGI-C (Manfioletti et al., 1991) (FIG. 8c). The HMGI members have been assigned multiple functions (Manfioletti et al., 1991) and recently, have been shown to play a critical role in regulation of gene expression as architectural factors by inducing DNA conformational changes in the formation of the three-dimensional transcription complex (Thanos & Maniatis, 1992; Du, W. et al., 1993).

Subsequently, the genomic structure of HMGI-C revealed that the gene contains five exons and spans a region of approximately 110 kb (FIG. 8d).

Single copy sequences from the 190 kb cloned pygmy locus, surrounding and including the HMGI-C gene (FIG. 8d), were used as probes on Southern blots containing DNA isolated from the two informative alleles (Xiang et al., 1990).

The genomic area encompassing HMGI-C is completely deleted in the transgenic insertional mutant pg$^{TgN40ACha}$ (A/A), whereas in the spontaneous mutant pg, the 5' sequences and the first two exons are absent (FIG. 8d).

Misexpression of Disrupted HMGI Proteins in Human Tumors

Cancer arises from aberrations in the genetic mechanisms that control growth and differentiation and ongoing elucidation of these mechanisms continues to improve the understanding of mammalian development and its various abnormalities. Increasingly, accumulating experimental evidence points towards transcriptional deregulation as one of the pivotal events in neoplasia. Many of the known transforming retroviral oncogenes, such as v-myc, v-fos and v-myb, are homologs of mammalian transcription factors which are normally involved in proliferation and differentiation control. Genes that encode for such transcription factors are frequently affected by the somatically acquired genetic changes which arise stochastically over a lifetime of an organism. These alterations, which can either activate expression of the relevant genes or disrupt them to create novel fusion proteins, affect transcription networks and initiate cancer.

One of the transcription factors whose disruption was shown to result in tumorigenesis is HMGI-C, which has attracted considerable attention for two reasons. First, a series of elegant experiments demonstrated that HMGI(Y) is involved in transcriptional regulation and is required for virus induction of the human interferon-β gene expression. These observations were incorporated into a novel model in which activation of gene expression is initiated by a higher order transcription enhancer complex. This functional nucleoprotein entity termed enhanceosome is formed when several distinct transcription factors assemble on DNA in a stereospecific manner. Combinatorial mechanisms of the enhanceosome formation enable the cell to achieve high specificity of gene activation in response to multiple biological stimuli. As an essential component of the enhanceosome, HMGI(Y) promotes the assembly of this three-dimensional structure through both protein-protein and protein-DNA interactions. The latter activity is mediated through the HMGI DNA-binding domains.

The function of HMGI-C, the other known member of the HMGI family, in growth and development control is better understood at the biological level. In humans, rearrangements of HMGI-C were linked to the pathogenesis of several distinct types of solid tumors. Rearrangements of the chromosomal band 12q13–15, consistently found in a wide variety of benign mesenchymal neoplasms, disrupt HMGI-C and generate novel chimeric transcripts. In the vast majority of the analyzed tumors, these transcripts consist of the HMGI-C DNA-binding domains fused to ectopic sequences provided by the translocation partner.

In the mouse, HMGI-C inactivation produced a dramatic disruption of both pre- and postnatal growth, resulting in the pygmy phenotype. Pygmy mice exhibit significant growth retardation which is first apparent in midgestation and becomes even more pronounced after birth. Adult animals are proportionally built and viable but exhibit a 60% weight reduction compared to their wildtype littermates. A detailed phenotypic analysis of the pygmy mouse revealed that the weight reduction in most of the tissues is commensurate with the overall decrease in body weight. Most interestingly, HMGI-C inactivation does not affect the growth hormone-insuline-like growth factor endocrine pathway, suggesting that HMGI-C functions in a previously unknown growth regulatory mechanism.

The molecular basis of the pygmy mutation is not well understood. High levels of the HMGI proteins are not required for cell growth per se and elevated HMGI expression appear to be associated with the biological state of the cell more directly than with its high proliferation rate. Upon transformation with oncogenic retroviruses, expression of HMGI-C and HMGI(Y) in epithelial cells is dramatically increased even though the proliferative capacity of the infected cells remains unaffected. Furthermore, analysis of a transformed cell line which retained its differentiated phenotype revealed that levels of the HMGI expression were significantly lower than in cell lines which lost their differentiation markers as a result of transformation. Other studies demonstrated that HMGI-C is expressed in less differentiated mesenchymal cells but is no longer present in their terminally differentiated counterparts. In combination, these results indicate that the function of the HMGI proteins may be to maintain the undifferentiated cellular state.

The diverse set of mesenchymal neoplasms in which HMGI-C is frequently disrupted by translocations of 12q13–15 includes lipomas, uterine leiomyoma, pulmonary hamartoma and pleomorphic adenomas of salivary gland. Another cytogenetic subgroup which can be identified in this set of tumors is characterized by rearrangements at 6p21–23. Intriguingly, HMGI(Y) has previously been localized to this chromosomal area.

Translocation Breakpoints Upstream of the HMGI-C Gene in Uterine Leiomyomata Uterine leiomyomata, also known as fibroids, are the most common pelvic tumors in women. Systematic histologic examination of hysterectomy specimens has shown a prevalence as high as 77% for these tumors in women of reproductive age. Although benign, uterine leiomyomata constitute a major health problem as they are associated with abnormal uterine bleeding, pelvic pain, urinary incontinence, spontaneous abortion, premature delivery, and infertility. Symptomatic fibroids are the leading indication for hysterectomy, accounting for 27% of the estimated 680,000 procedures performed annually in the United States.

Several different consistent chromosomal rearrangements have been identified in uterine leiomyomata, and they suggest involvement of a critical gene on chromosome 12 in the pathobiology. A translocation involving chromosomes 12 and 14, t(12;14)(q14–15;q23–24), represents one of the most common rearrangements, although trisomy 12, inversions and duplications of 12q14–q15, and translocations of 12q14–q15 with chromosomes other than 14 are not uncommon. The breakpoint in 12q14–q15 in uterine leiomyomata is in an intriguing chromosomal region because it is also the location of consistent rearrangements in other benign solid tumors, including lipomas and pleomorphic adenomas of the salivary gland. Rearrangements of 12q13–15 have been reported in pulmonary chondroid hamartoma, endometrial polyps, epithelial breast tumors, hemangiopericytoma, and an aggressive angiomyxoma. These tumors have the common properties of being mesenchyme-derived and benign. Therefore, it has been hypothesized that a single gene involved in mesenchyme differentiation and growth could be responsible for these multiple tumor types.

H. R. Asher et al. (1995) reported that HMGI-C, an architectural factor that functions in transcriptional regulation, is disrupted by rearrangement at 12q14–15 chromosomal breakpoint in lipomas and suggests a role for HMGI-C in adipogenesis and mesenchyme differentiation.

X. Zhou et al., (1995) shows that the pygmy phenotype arises from the inactivation of HMGI-C which function as architectural factors in the nuclear scaffold and are critical in the assembly of stereospecific transcriptional complexes.

SUMMARY OF THE INVENTION

The present invention pertains to a method for detecting HMGI-C or HMGI(Y) as a diagnostic marker for benign or malignant tumors using a probe for a sample, or an extract thereof, from a patient that recognizes HMGI-C or HMGI(Y), which comprises the steps of:

(a) contacting HMGI-C or HMGI(Y) from a sample from a patient with a probe which binds to HMGI-C or HMGI(Y); and (b) analyzing for HMGI-C or HMGI(Y) by detecting levels of the probe bound to the HMGI-C or HMGI(Y), wherein the presence of HMGI-C or HMGI(Y) in the sample is positive for a benign or malignant tumor.

The present invention also pertains to a method for detecting antibodies to HMGI-C or HMGI(Y) as a diagnostic marker for benign or malignant tumors using a probe for a sample, or an extract thereof, from a patient that recognizes antibodies to HMGI-C or HMGI(Y), which comprises the steps of:

(a) contacting antibodies to HMGI-C or HMGI(Y) from a sample from a patient with a probe which binds to antibodies to HMGI-C or HMGI(Y); and (b) analyzing for antibodies to HMGI-C or HMGI(Y) by detecting levels of the probe bound to the antibodies to HMGI-C or HMGI(Y), wherein the presence of antibodies to HMGI-C or HMGI(Y) in the sample is positive for a benign or malignant tumor.

The present invention further pertains to a method for treating benign and malignant tumors in a patient by blocking the biological activity of HMGI-C or HMGI(Y) which comprises adminstering to the patient a therapeutically effective amount of an inhibitor specific for HMGI-C or HMGI(Y).

The present invention still further pertains to a method for treating obesity in a patient by blocking the biological activity of HMGI-C or HMGI(Y) which comprises administering to the patient a therapeutically effective amount of an inhibitor specific for HMGI-C or HMGI(Y).

BRIEF DESCRIPTION OF THE FIGURES

FIGS. 1(A) and 1(B) illustrate the genomic structure of the human HMGI-C gene.

FIGS. 6(A) and 6(B) illustrate novel sequences fused to the DNA binding-domains of HMGI-C which encode transcriptional regulatory domains.

FIGS. 10(A) through (C) illustrate targeted disruption of the HMGI-C gene.

FIGS. 11(A) through (C) illustrate expression of HMGI-C in development and growth.

DETAILED DESCRIPTION OF THE INVENTION

Figure 2:
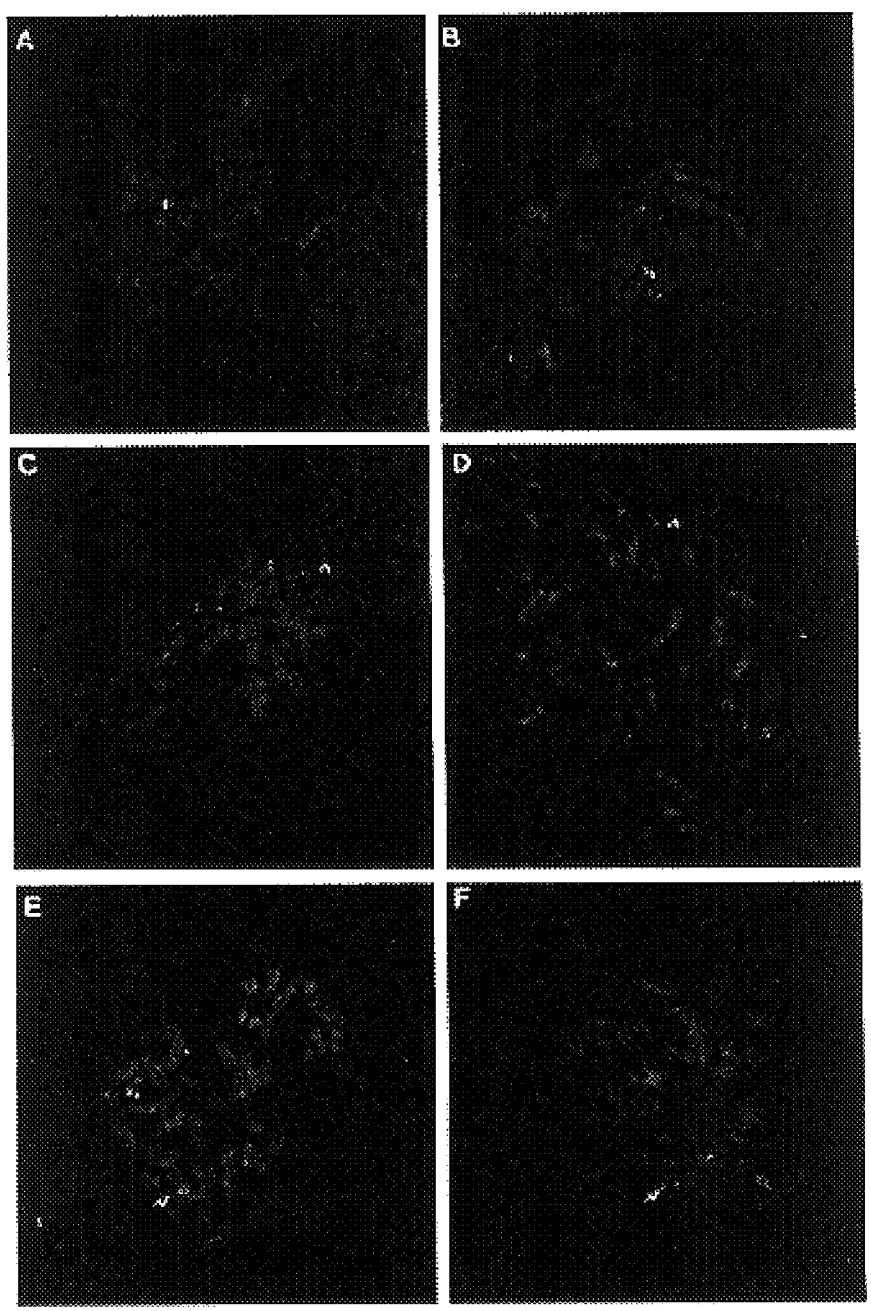
FIGS. 2(A) through 2(F) illustrate FISH mapping of HMGI-C lambda clones to lipoma tumor metaphase chromosomes from three lipomas revealing rearrangement of HMGI-C in all three tumors.

Aberrations in the genetic mechanisms that control growth and proliferation have emerged as a primary event in carcinogenesis. The function of HMGI-C and HMGI(Y), two embryonically expressed DNA-binding proteins, was investigated because their expression is highly associated with tumor development.

Disruptions of either HMGI-C or HMGI(Y) in humans result in a diverse array of solid mesenchymal tumors. Most prominent among these neoplasms are uterine leiomyomata, the most common pelvic tumors in women and the indication for over 200,000 hysterectomies annually in the United States. In tumors of mammary and thyroid glands as well as in prostate cancer, HMGI expression is highly correlated with tumor progression and metastasis, suggesting that these proteins can be used for as progression markers for a variety of tumor types.

Further proof for the pivotal role of HMGI proteins in both normal and pathological growth was obtained in the mouse system. Homologous recombination was used to inactivate murine HMGI-C gene. Demonstrating the importance of the HMGI genes in growth regulation, HMGI-C knockout mice exhibit significant growth retardation (mutant mice are 60% smaller than their wild-type littermates) with the reduction in most tissues commensurate with the overall decrease in the body weight. Even more importantly, these pygmy mice are highly resistant to chemically induced skin cancer. Specifically, the frequency of tumor development in the knockout mice is 40% of that in the control animals and tumor multiplicity exhibits a 20-fold decrease. Independently, inhibition of HMGI-C synthesis was shown to render thyroid epithelial cells intransigent to retroviral transformation. At the molecular level, HMGI proteins function in transcriptional regulation by promoting cooperative binding of the transcription factors to DNA. Deregulation of the downstream target genes can easily account for the important biological roles of the HMGI proteins as well as for the dramatic consequences of their inappropriate expression.

Lipomas are one of the most common mesenchymal neoplasms in humans. They are characterized by consistent cytogenetic aberrations involving chromosome 12 in bands q14–15. Interestingly, this region is also the site of rearrangement for other mesenchymally derived tumors. The present invention demonstrates that HMGI-C, an architectural factor that functions in transcriptional regulation, has been disrupted by rearrangement at the 12q14–15 chromosomal breakpoint in lipomas. Chimeric transcripts were isolated from two lipomas in which HMGI-C DNA-binding domains (A-T hook motifs) are fused to either a LIM or an acidic transactivation domain. These results identify the first gene rearranged in a benign neoplastic process that does not proceed to a malignancy and suggest a role for HMGI-C in adipogenesis and mesenchyme differentiation.

HMGI-C is an attractive candidate gene to be implicated in lipoma formation. This gene is required in transformation (Berlingieri et al., 1995) and is a transcriptional regulatory factor as are many genes identified at translocation breakpoints in a variety of tumors (Rabbitts, 1994). Secondly, disruption of HMGI-C leads to mice of small stature which, most intriguingly, have disproportionately less body fat than normal littermates (Benson and Chada, 1994). Finally, mouse HMGI-C maps to a region syntenic to human 12q14–15 which is the area most frequently rearranged in lipomas (Mandahl et al., 1988). Therefore, the human homolog of the mouse HMGI-C gene was cloned and its possible role in lipomas investigated.

Growth is one of the fundamental aspects in the development of an organism. Classical genetic studies have isolated four viable, spontaneous mouse mutants (Green, 1989) disrupted in growth, leading to dwarfism. Pygmy is unique among these mutants because its phenotype cannot be explained by aberrations in the growth hormone-insulin-like growth factor endocrine pathway (Lin, 1993; Li, et al., 1990; Sinha et al., 1979; Nissley et al., 1980). The present invention shows that the pygmy phenotype arises from the inactivation of HMGI-C and are critical in the assembly of stereospecific transcriptional complexes (Tjian & Maniatis, 1994). In addition, HMGI-C and the other HMGI family member, HMGI(Y)(Johnson et al., 1988), were found to be expressed predominantly during embryogenesis. The HMGI family are known to be regulated by cell cycle dependent phosphorylation which alters their DNA binding affinity (Reeves et al., 1991). Overall, these results demonstrate the important role of HMGI proteins in mammalian growth and development.

Among the most prominent characteristics consistently exhibited by cancer cells are karyotypic aberrations which disturb genes essential for the regulation of fundamental cellular processes. A wide array of solid mesenchymal tumors is characterized by recurrent rearrangements of chromosomal bands 12q13–15 or 6p21–23. This study shows that HMGI expression is normally restricted to undifferentiated, rapidly dividing cells but is activated in differentiated adipocytes following translocations of 12q13–15 or 6p21–23 in human lipomas. The present invention shows that the molecular pathway of tumor development is dictated by the precise nature of HMGI disruption and that HMGI misexpression in a differentiated cell is a pivotal event in benign tumorigenesis.

Uterine leiomyomata are the most common pelvic tumors in women and are the indication for more than 200,000 hysterectomies annually in the United States. Rearrangement of chromosome 12 in bands q14–q15 is characteristic of uterine leiomyomata and other benign mesenchymal tumors, and a YAC spanning chromosome 12 translocation breakpoints was identified in a uterine leiomyoma, pulmonary chondroid hamartoma, and lipoma. Recently, it was demonstrated that HMGI-C, an architectural factor mapping within the YAC, is disrupted in lipomas, resulting in novel fusion transcripts. This study concerns the localization of translocation breakpoints in seven uterine leiomyomata 10 to >100 kb upstream of HMGI-C by use of fluorescence in situ hybridization. These findings suggest a different pathobiologic mechanism in uterine leiomyomata from that in lipomas. HMGI-C is the first gene identified in chromosomal rearrangements in uterine leiomyomata and has important implications for an understanding of benign mesenchymal proliferation and differentiation.

Recently, molecular dissection of this chromosomal region has substantiated this hypothesis. To identify a gene at the breakpoint on chromosome 12 in uterine leiomyomata, a high-density physical map of the t(12;14) breakpoint region was constructed and identified a YAC, 981f11, that spans the translocation breakpoints in a uterine leiomyomata, pulmonary chondroid hamartoma and a lipoma. Further detailed characterization showed that the gene for HMGI-C, an architectural factor that is a non-histone component of chromatin, maps within 981f11 and is disrupted in lipomas. HMGI-C is rearranged in lipomas with chromosome 12 translocations, resulting in novel chimeric transcripts that fuse the DNA-binding A-T hook domains of HMGIC with potential transcriptional activation domains.

Furthermore, there is evidence that HMGI-C plays a role in mesenchymal cell proliferation.

RESULTS

HMGI Proteins in Adipogenesis and Mesenchyme Differentiation

Genomic Isolation and Characterization of the Human HMGI-C Gene

To obtain genomic clones of HMGI-C, DNA from yeast strains harboring YACs, yWPR383 and yWPR384 were subcloned into the lambda FIXII vector. Because there is extensive conservation (96%) between mouse and human HMGI-C homologs (Patel et al., 1994), mouse HMGI-C cDNA fragments encompassing all five exons were used as probes on lambda libraries and five clones were isolated (FIG. 1A). Restriction mapping of lambda clones followed by Southern blot analysis allowed identification of various restriction fragments containing cross-hybridizing sequences. These fragments were subcloned and nucleotide sequence analysis confirmed published data (Patel et al., 1994). The first three exons each contain a DNA binding domain encoding the A-T hook motif that is characteristic of the HMGI family (Reeves and Nissen, 1990) and exons 4 and 5 encode the acidic domain of the molecule (Manfioletti et al., 1991) (FIG. 1B). Notably, a large intron (>25 kb) between exons 3 and 4 separates the DNA binding domains from the remainder of the protein (FIG. 1B).

Fluorescence In Situ Hybridization of Lambda HMGI-C Exon Clones to Lipoma Metaphase Chromosomes Lambda clones from 5' and 3' ends of HMGI-C were used as probes for FISH to tumor metaphase chromosomes. In lipoma ST90–375 containing a t(12;15)(q15;q24) translocation, lambda clone H403 which contains the 5' end of the gene gave a hybridization signal on the der(12), thus mapping proximal to the breakpoint. In contrast, lambda clone H4002 which contains a portion of the 3' end of the HMGI-C gene, gave a hybridization signal on the der(15) and therefore maps distal to the breakpoint (FIG. 2). This result is consistent with a disruption of HMGI-C due to the t(12; 15) in this lipoma. Two other lipomas with translocations in 12q15 were studied, similarly. In ST93–724 containing a t(3;12)(q29;q15), lambda clone H409 containing the 5' end of HMGI-C hybridized to the der(12), while the 3' end clone H4002 hybridized to the der(3) (FIG. 2). In ST91 198 with a t(12;13)(q14–22;q21–32), the 5' clone H403 mapped on the der(13) suggesting a position distal to the breakpoint. However, from the 3' end, no hybridization to either derivative chromosome was noted in 20/20 metaphases using lambda clone H4002 indicating that this portion of HMGI-C is deleted (FIG. 2). Therefore, in this tumor, the translocation appears to be proximal to HMGI-C with the 5' end of the gene retained but the 3' end deleted. Regardless of the chromosomal mechanism which may include a complex rearrangment in ST91198, HMGI-C is disrupted in three out of three lipomas analyzed.

Identification of Chimeric Transcripts

Figure 3:
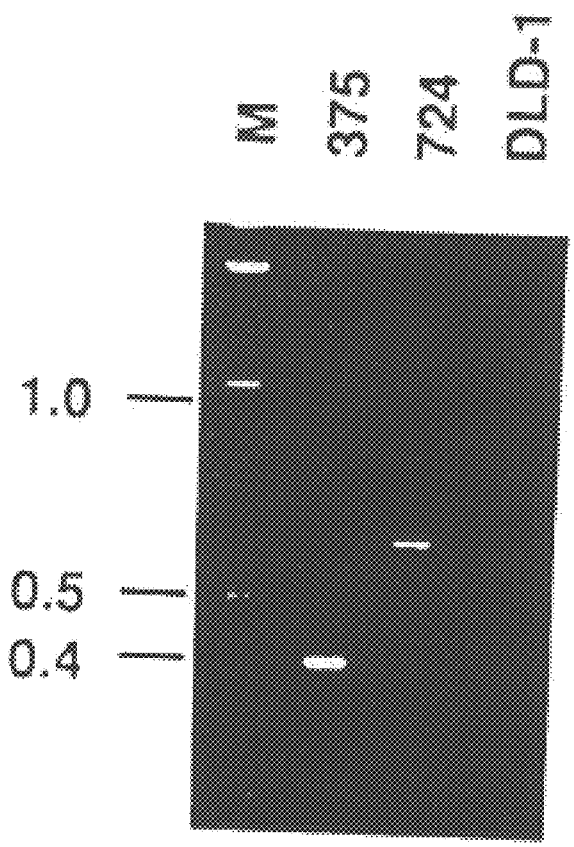
FIG. 3 illustrates RT-PCR amplification of HMGI-C chimeric transcripts.

The molecular structure of the HMGI-C transcripts in the lipomas was next investigated. Total mRNA was isolated (Chirgwin et al., 1979) from primary cell cultures of ST90–375 t(12;15) and ST93–724 t(3;12) and 3' RACE performed (Frohman et al., 1988). The resulting products were analyzed by agarose gel electrophoresis and DNA fragments of size 441 and 627 bp were obtained from RNA samples isolated from ST90–375 and ST93–724, respectively (FIG. 3). These two DNA fragments were purified, subcloned and sequenced.

Figure 4:
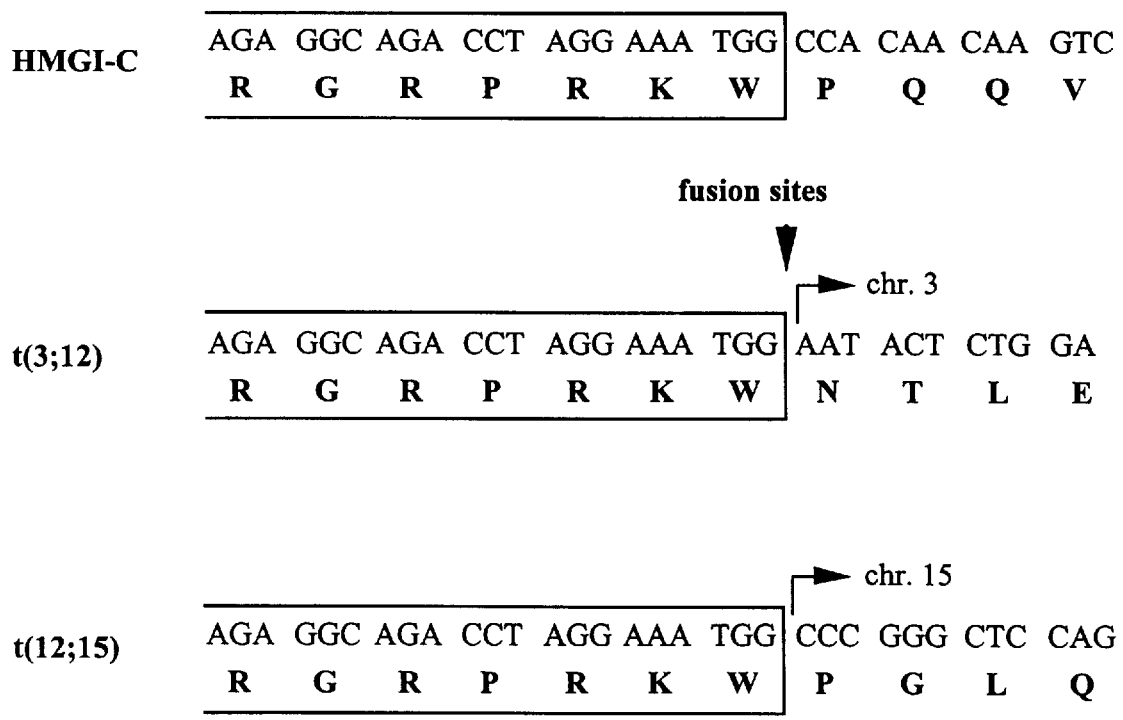
FIGS. 4(*a*) through 4(*c*) illustrates rearrangements of 12q15 in human lipomas which disrupt the HMGI-C gene and produce chimeric transcripts.

In both cases, sequence analysis revealed an in frame fusion of novel sequences to HMGI-C. These sequences differed between the two lipomas, and immediately followed exon 3 of HMGI-C (FIG. 4).

Figure 5:
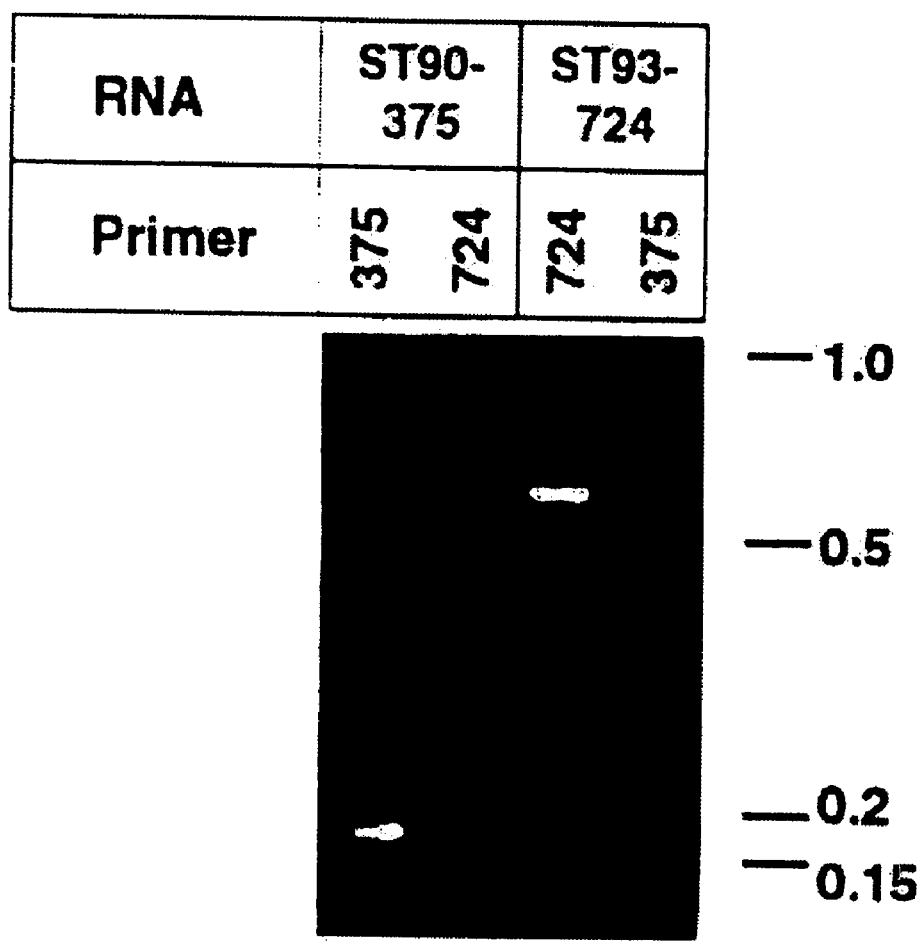
FIG. 5 illustrates RT-PCR using primers located on either side of the fusion site between HMGI-C and novel sequences.

The presence and specificity of chimeric transcripts in the two lipomas were confirmed further by an independent RT-PCR. cDNA was prepared from lipoma RNA samples but primers from the novel sequences, instead of oligo-dT, were used for the reverse transcription reaction so that only RNA transcripts spanning the translocation would result in a PCR amplification product (FIG. 5). Products of the predicted size were observed only when primers derived from the novel sequences were used to reverse transcribe RNA isolated from the corresponding cell lines. No products were seen in lipoma RNA from ST90–375 or ST93–724 when primers 724 or 375 were used, respectively.

Finally, the chromosomal origin of the novel sequences was determined using DNA prepared from a monochromosomal rodent-human somatic cell hybrid panel. Specific primers were designed for the two novel sequences obtained from the lipoma cDNAs. PCR performed on genomic DNA from the somatic cell hybrids demonstrated that the novel sequence fused to HMGI-C in ST93–724, with a t(3;12), was located on chromosome 3 (FIG. 6) and the novel sequence from ST90–375, with a t(12;15), mapped to chromosome 15 (FIG. 6).

Novel Sequences Encode for Transcriptional Regulatory Domains

A detailed computer analysis of the novel sequences from the two amplified fusion transcripts demonstrated that they encode putative transcriptional regulatory domains. Inspection of the predicted protein sequence from ST93–724 revealed the presence of two tandemly arrayed LIM domains (Sanchez-Garcia and Rabbitts, 1993) separated by the characteristic 8–10 amino acids (FIG. 6A). These domains are 50–60 amino acid residue motifs which are rich in cysteine and histidine and were first identified in three proteins, lin-11, Isl-1 and mec-3 (Way and Chalfie, 1988; Freyd et al., 1990; Karlsson et al., 1990). The domain is organized into two adjacent zinc fingers separated by a two residue linker (Feuerstein et al., 1994) and members of the LIM family of proteins may contain one or more LIM domains (Sánchez-Garcia et al., 1993). Many of the LIM-containing proteins are transcription factors (Sánchez-García et al., 1993) and their activity is thought to be regulated by protein-protein interactions through the ability of LIM domains to dimerize (Feuerstein et al., 1994).

Computer analysis of the novel sequence from ST90–375 did not reveal any significant homology with known sequences. Notably, the carboxy-terminal end of the predicted protein is highly acidic (pI 4.6) and rich in serine and threonine residues. Such domains have been implicated in transcriptional activation and have been shown to stimulate transcription from remote as well as proximal positions (Mitchell and Tijan, 1989; Seipel et al., 1992).

Figure 7:
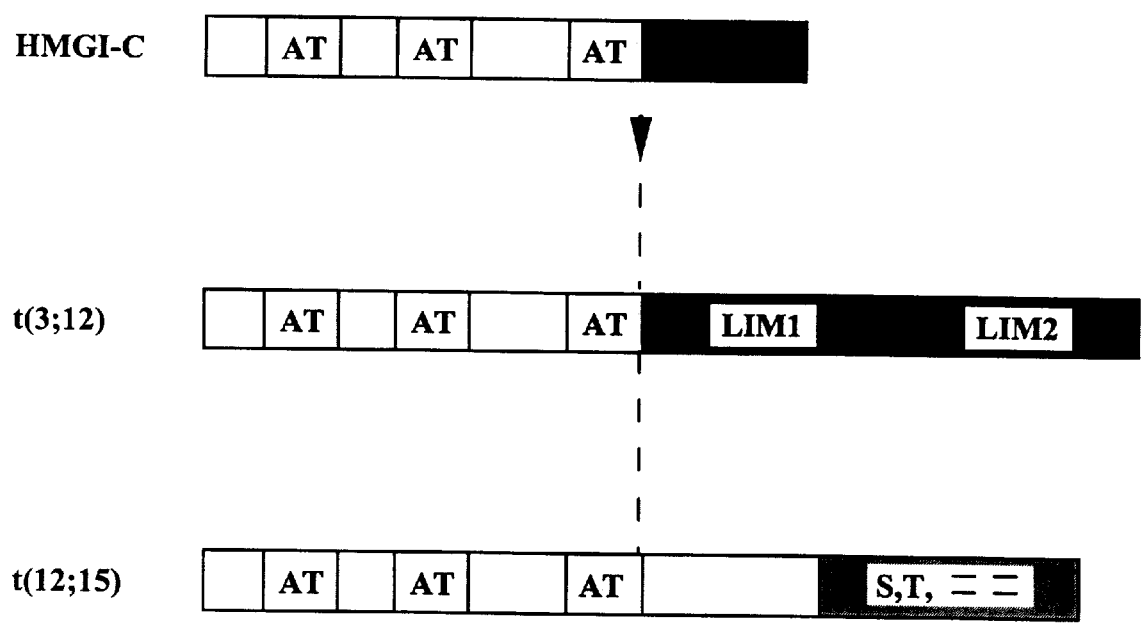
FIGS. 7(*a*) through 7(*c*) illustrates the structure and domain organization of HMGI-C and the predicted fusion proteins.

Therefore, the predicted domain organization of the wild-type HMGI-C and the fusion proteins can be schematically depicted as shown in FIG. 7. In both fusion proteins, the C-terminal domain of the wildtype HMGI-C, which does not activate transcription (Thanos and Maniatis, 1992; X.Z. and K.C., unpublished data) is replaced by distinct, potential transcription regulation domains. These newly acquired functional domains in combination with the A-T hooks of HMGI-C would give rise to unique proteins that may contribute to the pathobiology of lipomas.

HMGI Proteins in Mammalian Growth and Development

Figure 9:
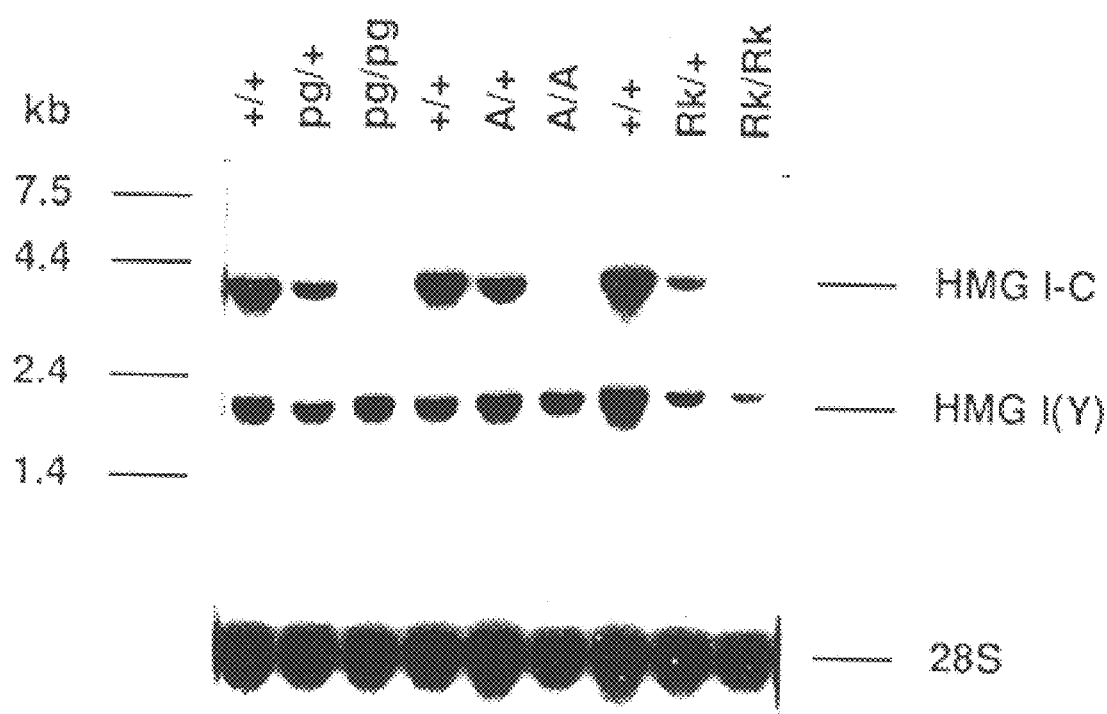
FIG. 9 illustrates HMGI-C gene expression of three alleles at the mouse pygmy locus.

Previous studies (King, J., 1955) had established that the pygmy phenotype could be observed at birth. Therefore, RNA from wildtype mouse embryos was isolated (Chirgwin, J. et al., 1979) and Northern blot analysis revealed a transcript of 4.1 kb (FIG. 9). As expected from the genomic analysis, no detectable HMGI-C expression was observed in the spontaneous and transgenic insertional mouse mutants. Additionally, a third allele exists at the pygmy locus (Green, M. C., 1989), In(10)17Rk, which carries an inversion of chromosome 10 and the distal breakpoint is within intron 3 of the HMGI-C gene (data not shown).

No HMGI-C expression was detected in homozygous embryonic In(10)17Rk RNA (FIG. 9). Quantitation by phosphorimager analysis revealed that heterozygous mice expressed HMGI-C at approximately 50% wildtype levels. Therefore, the wildtype allele in the heterozygous mice does not increase its expression levels to compensate for the loss of the deleted allele. This is consistent with the pygmy mutation being semi-dominant because there is a mild phenotypic effect on heterozygous mice (80% the weight of wildtype mice) (Benson, K. & Chada, K., 1994). Furthermore, HMGI(Y), the only other known member of the HMGI gene family (Grosschedl, R. et al., 1994), retained the same levels of expression in the mutant and wildtype mice (FIG. 9). Therefore, there is no compensation by HMGI(Y) for the lack of HMGI-C expression in pygmy mice.

The mutant alleles described above arise from major disruptions of genomic DNA which result in large deletions or a chromosomal inversion. To exclude the possibility that a gene other than HMGI-C may be responsible for the pygmy phenotype, a mouse null mutant of HMGI-C was produced by targeted disruption. Mouse embryonic stem (ES) cells were generated that had 3.0 kb of the HMGI-C gene, encompassing exons 1 and 2, replaced with a neomycin-resistance gene (FIG. 10(A)). Matings between mice heterozygous for the mutated allele produced mice homozygous for the disrupted allele (FIG. 10(B)) at the expected Mendelian frequency of approximately 25% (13/51). Immunoblot analysis demonstrated an absence of HMGI-C in protein extracts from homozygous embryos (FIG. 10(C)). Homozygous HMGI-C$^{-/-}$ mice revealed the classical features of the pygmy phenotype which include reduced birthweight, craniofacial defects (shortened head) and an adult body weight of approximately 40% (39.8 +/−2.9) of wildtype littermates (Benson, K. & Chada, K., 1994). Therefore, it can be concluded that absence of HMGI-C expression in mice causes the pygmy phenotype.

Previously, a restricted number of adult tissues were analysed (Manfioletti, G. et al., 1991) and established that the endogenous expression of HMGI-C could not be detected. Hence, a more comprehensive panel of tissues were examined to investigate the temporal and tissue specific expression pattern of HMGI-C. Within the sensitivity of Northern blot analysis, HMGI-C expression was not detected in 18 adult tissues (data not shown). However, expression of HMGI-C was observed during mouse embryogenesis (FIG. 1(A)) as early as 10.5 days post coitum (dpc), but essentially disappeared by 15.5 dpc. Remarkably, the other family member, HMGI(Y), showed a similar endogenous expression pattern (FIG. 11(A)) with expression readily observed in 10.5–16.5 dpc mouse embryos. The predominant expression of HMGI-C and HMGI(Y) during embryogenesis suggests this architectural factor family functions mainly in mammalian development.

The analysis of HMGI-C expression was further extended by its localization in the normal developing mouse embryo. Expression was observed in the majority of tissues and organs during embryogenesis as exemplified by the 11.5 dpc mouse embryo (FIG. 11(B)). Noticeably, HMGI-C expression was not seen in the embryonic brain except in a small, localized region of the forebrain (FIG. 11(B)). This expression pattern coincides with previous studies which demonstrated that most tissues in pygmy mice were 40–50% smaller as compared to wildtype tissues and the only tissue of normal size was found to be the brain (Benson, K. & Chada, K., 1994).

To initiate studies on the elucidation of the role of HMGI-C in cell growth, embryonic fibroblasts were cultured from homozygous and wildtype embryos. Strikingly, the number of pg/pg embryonic fibroblasts was four-fold less as compared to wildtype fibroblasts after four days in vitro (FIG. 11(C)) and was not due to cell death. This data, as well as similar studies in other systems (Ram, T. et al., 1993; Berlingieri, M. T. et al., 1995), is consistent with a role for HMGI-C in cell proliferation and suggests that HMGI-C functions in a cell autonomous manner. Furthermore, absence of HMGI-C expression in the pygmy mutant would then lead to a decrease in cell proliferation and causes the reduced size of all the tissues except for the brain.

Misexpression of Disrupted HMGI Proteins in Human Tumors

Isolation and Analysis of the Aberrant HMGI Transcripts

Rearrangements of HMGI-C in human tumors always preserve the DNA-binding domains of the protein and the DNA-binding activity of the HMGI architectural factors is essential for the enhancer activation. Moreover, sequence analysis demonstrated that the DNA-binding domains are completely conserved between human HMGI-C and HMGI (Y) (Figure not shown). Therefore, HMGI expression was investigated in human tumors with karyotypic abnormalities involving chromosomal band 6p21–23.

Establishment of cell lines is frequently associated with accumulation of mutations in vitro. To exclude such artifacts, RNA was isolated directly from frozen tumor samples. Lipomas ST92–24269 t(4;6) and ST88–08203 t(6;11) were karyotyped and total RNA was purified from frozen tissues by cesium chloride centrifugation. Next, amplification of the HMGI transcripts was performed using 3' RACE protocol. Upon analysis of the resulting reactions by gel electrophoresis, aberrant HMGI(Y) products were readily detectable (Figure not shown). At the same time, HMGI-C expression was not detected in these tumors (Figure not shown).

The anomalous HMGI(Y) cDNAs were further characterized by sequence analysis. In lipoma ST92–24269, the transcript encoded for the 5' end of HMGI(Y) followed by a novel sequence (Figure not shown). Comparison of this latter sequence to the Genbank database revealed that it was derived from the 3' UTR of wild-type HMGI(Y). PCR analysis of the genomic DNA from tumor ST92–24269 determined the transcript was produced by an internal deletion of both exonic and intronic sequences (unpublished data) which removed 922 bp from the wild-type HMGI(Y) cDNA (Figure not shown).

Sequencing of the aberrant transcript in lipoma ST88–08203 revealed a fully intact HMGI(Y) open reading frame. A detailed molecular analysis demonstrated that this transcript was produced by the removal of 923 bp of the wild-type sequence from exon 8 (Figure not shown). Interestingly, the rearrangement was limited to the 3' UTR of the gene, leaving the coding sequence intact. Therefore, the aberrant transcripts isolated from the lipomas with rearrangements of 6p21 are produced by internal deletions within the HMGI(Y) gene. The findings in both tumors were confirmed by an independent RT-PCR in which an HMGI (Y)-specific reverse primer rather than oligo-(dT) was used for reverse transcription and subsequent PCR (Figure not shown).

In lipoma ST92–24269, the predicted HMGI(Y) fusion protein consists of the first two DNA-binding domains of HMGI(Y) fused in frame to an uninterrupted open reading frame (ORF) encoding for 108 amino acid residues. A detailed examination of the ORF revealed an unusually high content of proline (17%) which is indicative of a potential transcriptional regulatory domain (Figure not shown). Therefore, the overall structure of this HMGI(Y) fusion protein is remarkably similar to proteins produced by disruptions at 12q13–15 which juxtaposed DNA-binding domains of HMGI-C to putative transcriptional regulatory domains.

Translation of the HMGI(Y) aberrant transcript in the tumor ST88–08203 predicted a normal protein. In contrast, in previously described lipomas chimeric HMGI-C transcripts encoded for novel fusion proteins whose formation was proposed to be necessary for lipoma development. To establish whether differences in the overall domain organization of the HMGI(Y) and HMGI-C fusion proteins found in lipomas are due to the distinct properties of these two genes, an additional tumor with HMGI-C rearrangement, lipoma ST91–198 t(12;15), was analyzed. RNA was isolated from the primary cell culture and 3' RACE used to amplify the HMGI-C chimeric transcript (unpublished data). The molecular analysis of this cDNA revealed that it preserved the first three exons of HMGI-C that encode for the HMGI DNA-binding domains. However, the endogenous HMGI exons four and five were removed and replaced by a heterologous sequence (Figure not shown). Notably, an in-frame stop codon present in this sequence terminates translation of the chimeric transcript after adding only ten amino acid residues to the HMGI-C DNA-binding domains. The sequence of the novel peptide did not contain any distinguishing features and revealed no significant homology with known proteins. Chromosomal rearrangement in tumor ST91–198 therefore results in a truncated protein that consists mainly of the HMGI-C AT-hooks. Accordingly, a simple truncation of either HMGI(Y) or HMGI-C is sufficient to cause lipomas.

Lipomas Can Bypass Expression of the Wild-type HMGI Allele Expression of the wildtype HMGI proteins is highly associated with transformation and can be detected in a wide variety of tumors. Moreover, inhibition of HMGI-C synthesis was shown to render several distinct cell types intransigent to retroviral transformation, suggesting that HMGI expression is required for tumorigenesis. Appreciable levels of wild-type HMGI(Y) expression that were found in tumor ST88–08203 (Figures not shown) are in agreement with this hypothesis. Surprisingly, the non-rearranged allele was not expressed in lipoma ST92–24269 (Figures not shown) where an HMGI(Y) fusion protein was identified.

In lipomas with rearrangements of 12q13–15, chimeric transcripts are produced by the juxtaposition of HMGI-C with the heterologous sequences and therefore cannot be readily amplified in the same PCR reaction with the wild-type cDNA. To assess the expression of the wild-type HMGI-C in these tumors, the highly polymorphic microsatellite sequence located in the 5' UTR of HMGI-C was employed. Oligonucleotide primers complimentary to the sequences flanking this polypyrimidine tract were synthesized and used for RT-PCR (Figure not shown). Again, expression from the non-rearranged allele was only observed in the tumor with a truncated HMGI-C. No expression of the wildtype allele but not in the lipoma ST93–724, in which HMGI-C DNA-binding domains were fused to LIM domains, motifs that function in transcriptional regulation (Figure not shown).

Differentiated Adipocytes Express HMGI-C in Lipomas but not in Normal Fat

During development, the expression of the HMGI proteins is tightly regulated. HMGI expression is found in the developing tissues and organs of the mouse embryo but essentially dissapears by the end of intrauterine development and can no longer be found postnatally. To confirm that HMGI expression in lipomas is not a consequence of the endogenous HMGI expression by the adult adipose tissue, immunocytochemistry was performed with an antibody raised against HMGI-C. In full agreement with numerous previous findings which demonstrated that HMGI proteins are not expressed by differentiated cells or adult tissues, HMGI-C expression could not be detected in the adult adipose tissue (Figure not shown). Futhermore, RT-PCR with primers specific for HMGI-C and HMGI(Y) confirmed that HMGI genes are not expressed in normal fat (unpublished data). However, the majority of differentiated adipocytes in these neoplasms stained positively for HMGI-C (Figure not shown). Overall, HMGI-C expression was detected in 75% (22 out of 29) of tumors (unpublished data).

Translocation Breakpoints Upstream of the HMGI-C Gene in Uterine Leiomyomata

FISH analysis was performed on metaphase cells from uterine leiomyomata with chromosome 12 rearrangements (Table not shown) by use of clones from the 5' and 3' ends of HMGI-C (Figure not shown). In contrast to lipomas, where translocation occurs in frame following exon 3, both 5' and 3' clones hybridized only, on the rearranged chromosome not derived from chromosome 12, in addition to the normal 12 homolog, indicating that the entire sequence encoding HMGI-C maps distal to the translocation breakpoint. In two uterine leiomyomata with typical t(12,14) translocations (ST90–194 and ST93–738), breakpoints mapped within the same lambda clones approximately 10 kb upstream of exon 1 of HMGI-C (Figures not shown). These breakpoints were verified by Southern blot analysis, a 3.3 kb probe from lambda clone H528 detected rearranged bands in both tumors (unpublished data). In ST92–224, a uterine leiomyoma with a variant translocation involving chromosome 1, the breakpoint mapped within this same region, indicating that this site on chromosome 12 contains a critical region for rearrangement regardless of the chromosomal origin of the translocated material. FISH analysis of ST94–114, another uterine leiomyoma with a characteristic t(12;14) revealed a breakpoint approximately 100 kb 5' of HMGIC. In two other uterine leiomyomata (ST93–165 and ST89–171), breakpoints occurred more than 100 kb upstream of HMGI-C as the most 5' lambda clone in the contig (H121) is translocated to the der(14) chromosome in these tumors. ST89–171 contains two normal chromosome 12 homologs in addition to a der(14)t(12;14); therefore, hybridization signals corresponding to three copies of HMGI-C were detected (Figure not shown). Finally, another uterine leiomyoma (ST93–220) with an atypical cytogenetic rearrangement in which the involved segment of chromosome 12 appeared to be proximal in band q13 was determined by FISH to have a deletion starting approximately 10 kb upstream of HMGI-C and extending up to about 100 kb 5' of exon 1 of HMGI-C (Figure not shown).

DISCUSSION

HMGI Proteins in Adipogenesis and Mesenchyme Differentiation

In this study, chimeric transcripts were identified from two lipomas which resulted from fusion of the 5' end of the HMGI-C gene to novel sequences derived from different chromosomes. Three DNA binding domains containing the A-T hook motifs of HMGI-C are linked in these transcripts to sequences encoding potential transcriptional regulatory domains. In the case of lipoma ST90–375, the novel domain is highly acidic and rich in serine and threonine residues resembling the typical activation domains found in transcription factors. In lipoma ST93–724, the novel protein contains two LIM domains, motifs that promote protein-protein interactions.

HMGI-C, Chimeric Transcripts and Lipomas

The chromosomal region 12q14–15 is hypothesized to contain an important gene involved in lipomas because it is the most commonly rearranged site (Mandahl et al., 1988). Our study establishes that HMGI-C is the gene disrupted in lipomas with chromosome 12 rearrangments. The large intron (greater than 25 kb) between exons 3 and 4 distinctly separates the DNA-binding from the acidic domains of HMGI-C. This provides a substantial target for translocations so that the three A-T hook motifs remain intact and confer the DNA-binding specificity of HMGI-C to the fusion proteins.

HMGI-C is a 109 amino acid residue protein (Patel et al., 1994) that consists of three DNA-binding domains (A-T hooks) linked to the carboxy-terminal acidic domain which does not activate transcription (Thanos and Maniatis, 1992; X. Z. and K. C., unpublished data). The two lipoma translocations result in a novel protein containing A-T hooks of HMGI-C at the amino-terminus fused to transcriptional regulatory domains at the carboxy end. The other reported example for an A-T hook containing gene implicated in tumorigenesis is MLL (Tkachuk et al., 1992; Gu et al., 1992). However, the presence of a putative second DNA20 binding domain (Ma et al., 1993) derived from the MLL gene and retained in the fusion protein obscures the exact contribution of the A-T hooks to tumor pathogenesis (Rabbitts, 1994). In these lipomas, the only known HMGI-C functional domains retained in the fusion proteins are the A-T hooks. These motifs would therefore be responsible for DNA binding specificity of the fusion proteins. Although it is possible that simple truncation of HMGI-C is sufficient to cause lipomas, a number of studies have determined that both domains of fusion proteins are necessary for transforming activity (de The et al., 1991; Kamps et al., 1991;

Pendergast et al., 1991; May et al., 1993). Therefore, as proposed for other fusion proteins, the heterologous sequence in the lipoma fusion proteins would alter the biological activity of wildtype HMGI-C and lead to deregulation of downstream target genes.

The above model readily explains how the fusion protein produced in lipoma ST90–375 may function. The novel sequence from chromosome 15 encodes for an acidic peptide rich in serine and threonine residues. These features have been observed in a number of transcriptional activation domains (Mitchell and Tijan, 1989) including the carboxy-terminal domains of homeobox proteins (Hatano et al., 1991) and NF-KB (Schmitz and Baeuerle, 1991). So, the acquisition of a transactivation domain by the DNA-binding domains of HMGI-C, which normally possesses a transcriptionally inactive acidic domain, can easily be reconciled with aberrant regulation of the HMGI-C target genes. In the case of the t(3;12) in ST93–724, the fusion protein must operate by a different mechanism to deregulate the HMGI-C target genes. The novel sequence from chromosome 3 encodes for two tandemly arranged LIM motifs. The LIM domain is conserved amongst highly diverged species and LIM proteins have been shown to have important developmental functions which include patterning (Cohen et al., 1992), cell fate decision (Freyd et al., 1990) and differentiation (Way and Chalfie, 1988). LIM domain proteins are capable of protein-protein interactions (Sadler et al., 1992) through dimerization mediated by the LIM domains (Feuerstein et al., 1994). Therefore, LIM-LIM interactions between the ST93–724 fusion product and other nuclear proteins could recruit potential transcriptional regulators to DNA sequences with a specificity dictated by the HMGI-C A-T hook motifs. Deregulation of HMGI-C target genes would then contribute to lipoma development. It is interesting to note that the majority of nuclear proteins capable of interacting with LIM domains are known to function as transcription factors. These include several LIM-homeodomain proteins (Sanchez-Garcia et al., 1993 and references within) as well as basic helix-loop-helix proteins shPan-1 (German et al., 1992) and TAL1 (Valge-Archer et al., 1994). While overexpression of LIM proteins has been implicated in T-cell lymphomas (reviewed by Sanchez-Garcia and Rabbits, 1993), this is the first example of a LIM domain occurring in a fusion product.

A great heterogeneity in chromosomal partners translocated with 12q14–15 is found in karyotypically abnormal lipomas indicating that a large number of sequences in the genome can be fused to HMGI-C. The present data demonstrate that novel sequences linked to HMGI-C in two lipomas encode for distinct domains. This suggests that a number of alternative domains can be placed downstream of the HMGI-C A-T hooks and contribute to the pathobiology of lipomas. Interestingly, both novel sequences described in this study encode for transcriptional regulatory domains. Therefore, the choice of novel sequences in chimeric transcripts in lipomas is presumably not arbitrary but does require the presence of regulatory transcriptional domains attached to the HMGI-C A-T hooks.

A similar situation has been observed in the 11 q23 acute leukemias where the MLL gene is translocated with multiple chromosomal partners which mostly encode different types of transcriptional regulatory domains (Prasad et al., 1994). This could be a general mechanism for tumors where nonrandom rearrangements of a specific chromosomal region involve a variety of partners. Chimeric transcription factors that promote tumorigenesis would be produced by juxtaposing DNA binding domain(s) contributed by the consistently rearranged locus to distinct types of transcriptional regulatory domains.

HMGI-C, Pygmy and Adipogenesis

The above studies demonstrate that an altered HMGI-C protein is involved in the abnormal growth and development of fat cells resulting in lipomas. This leads to the possibility that HMGI-C may normally play a role in adipogenesis and analysis of the pygmy mouse strongly substantiates this hypothesis. The mouse mutant, pygmy, was found to be a null mutation of HMGI-C due to deletions within the gene (unpublished results). The obvious phenotypic characteristics of the pygmy mouse are its small stature with most tissues reduced commensurate with the overall decrease in weight of the mouse (40% of wildtype). Interestingly, one tissue disproportionately reduced in weight is body fat. The fat index, a reliable indicator of total fat content relative to body weight (Rogers and Webb, 1980), is approximately eight times lower in pygmy than in their wild-type littermates (Benson and Chada, 1994). The function of HMGI-C in adipogenesis could be related to its role in cells undergoing differentiation. It is expressed in less differentiated cells but no detectable levels are observed in their terminally differentiated counterparts (Vartainen et al., 1988; Giancotti et al., 1987).

Therefore, lack of HMGI-C expression, as found in the pygmy mouse, could affect the differentiation of preadipocytes into mature adipocytes, cells capable of lipid storage. This developmental abnormality would lead to a decrease in fat deposition and the phenotype observed in the pygmy mouse. The role of HMGI-C in adipogenesis and metabolic disorders such as obesity is thus of considerable interest.

Relevance of HMGI Family in Tumors with Rearrangements of 12q13–15 or 6p21

Of major importance is the frequent observation of chromosomal rearrangements in bands 12q13–15 in a large group of benign solid tumors. Most prominently, these include uterine leiomyomata (Nilbert and Heim, 1990; Rein et al., 1991), and pleomorphic adenomas of the salivary gland (Sandros et al., 1990; Bullerdiek et al., 1993). Rearrangements of 12q13–15 have also been reported in pulmonary chondroid hamartomas (Dal Cin et al., 1993; Fletcher et al., 1995), endometrial polyps (Vanni et al., 1993), epithelial breast tumors (Rohen et al., 1993), hemangiopericytoma (Mandahl et al., 1993a), chondromatous tumors (Mandahl et al., 1989, 1993b; Bridge et al., 1992; Hirabayashi et al., 1992), diffuse astrocytomas (Jenkins et al., 1989), parosteal lipoma (Bridge et al., 1995), and a giant-cell tumor of the bone (Noguera et al., 1989). Many of these tumor types are of mesenchymal origin and it has therefore been hypothesized that a single gene associated with growth and mesenchyme may be responsible for these multiple neoplasms (Schoenberg Fejzo et al., 1995). Several lines of evidence implicate HMGI-C as a strong candidate for such a gene at 12q14–15. First, physical mapping studies have shown chromosomal breakpoints for three of these benign tumors (lipoma, pulmonary chondroid hamartoma and uterine leiomyoma) to map within a single YAC (Schoenberg Fejzo et al., 1995). This study assigns HMGI-C to the translocation breakpoint in lipomas, and chromosomal breakpoints in five analyzed uterine leiomyomata as well as a pulmonary chondroid hamartoma have been found to reside within 10–100 kb of exon 1 of HMGI-C (unpublished results). Second, the role of HMGI-C in growth control is apparent because its disruption in the pygmy mouse leads to aberrant growth and development. Also, it has been shown in vitro that HMGI-C is required for transformation (Berlingieri et al., 1995). Finally, preliminary studies reveal that expression of HMGI-C during mouse embryogenesis is restricted mainly to the mesenchymal component of tissues and organs (unpublished results). Taken together, these data indicate that HMGI-C is highly likely to be the gene disturbed by 12q14–15 rearrangements in a number of tumors of mesenchymal origin.

Nonrandom involvement of 6p21–23 has also been observed in lipomas (Sreekantaiah et al., 1991), pulmonary chondroid hamartomas (Fletcher et al., 1992, 1995) and uterine leiomyomata (Nilbert et al., 1990). Interestingly, HMGI(Y), the other member of the HMGI protein family with a similar structure as HMGI-C that includes the three DNA-binding domains, has been localized to 6p21 (Friedmann et al., 1993). This raises an intriguing possibility that HMGI(Y), a molecule closely related to, but distinct from HMGI-C, could also be associated with benign tumors of mesenchymal origin.

In summary, a disruption of the HMGI-C gene resulting in chimeric transcripts is a characteristic feature of lipomas. As adipocytes play a key role in lipid homeostasis and maintenance of energy balance in vertebrates, an understanding of HMGI-C function in adipogenesis may lead to insights into obesity and other metabolic disorders. In addition, the obvious role of HMGI-C in normal growth demonstrated by the phenotype of the pygmy mouse and its localization at or adjacent to the translocation breakpoints in lipoma, uterine leiomyoma and pulmonary chondroid hamartoma suggests its fundamental involvement in a variety of benign tumors.

HMGI Proteins in Mammalian Growth and Development

The current study demonstrates that the absence of HMGI-C causes growth retardation in pygmy mice. Although the precise molecular mechanism remains to be elucidated, the function of HMGI proteins in cell proliferation could be regulated during the cell cycle through alteration of their DNA binding ability via phosphorylation by the cell cycle-dependent p34cdc2 kinase (Reeves, R. et al., 1991). Inactivation of the HMGI-C gene would perturb the cell cycle in the developing embryo and the resulting disruption of growth would produce the pygmy phenotype. The identification of the pygmy gene as HMGI-C provides novel insights into the control of mammalian growth and development and a molecular clue to investigate the biochemical nature of the African pygmy phenotype (Sinha, Y. et al., 1979) and a multitude of growth hormone-resistant human dwarf syndromes (Benson, K. & Chada, K., 1994).

Misexpression of Disrupted HMGI Proteins in Human Tumors

HMGI(Y) and HMGI-C, two homologous but distinct members of the HMGI family of architectural factors, have now been shown to be disrupted in identical tumors. Rearrangements of HMGI-C, first reported in lipomas, were later described in other mesenchymally derived neoplasms with translocations of 12q13–15. Similar to HMGI-C, disruptions of HMGI(Y) will presumably be also responsible for uterine leiomyoma, pulmonary hamartoma, pleomorphic adenomas of salivary gland and other mesenchymal tumors with recurrent aberrations at 6p21–23.

Rearrangements within HMGI Genes are Required for Lipoma Development

In combination with previous studies on HMGI(C) and HMGI-Y, it is now possible to glean novel insight into the molecular mechanism of tumor formation in lipomas and, by extrapolation, in related solid mesenchymal neoplasms. HMGI-C does not behave as a classical transforming oncogene since overexpression of full-length HMGI-C cDNA does not result in tumorigenesis. On the other hand, in all twelve analyzed lipomas, chromosomal rearrangements have produced disruptions in translocated HMGI alleles. While expression of an HMGI gene is necessary for tumorigenesis, activation of an intact HMGI allele in a mesenchymal cell will not be sufficient to produce a tumor. Therefore, disruptions within HMGI genes and the aberrant structure of the resulting cDNA are required for lipoma development.

A variety of the HMGI chimeric transcripts can be found in lipomas. The comparison of these aberrant cDNAs demonstrates that rearrangements can range from a simple internal deletion to protein truncation to juxtaposition of transcriptional regulatory domains to HMGI DNA-binding domains. An aberration common to these twelve lipomas is a deletion of or within highly conserved and unusually large and 3' UTR of an HMGI gene. The best example is lipoma ST8808203, where the aberrant transcript codes for the wild-type HMGI(Y) and the deletion is limited to its 3' UTR. Since translocations of 12q13–15 which disrupt 3' UTR of HMGI-C while preserving its ORF are also observed in leiomyoma and pleomorphic adenoma of salivary gland, 3' UTRs of HMGI genes may contain important regulatory sequences that function in growth regulation and/or tumor suppression.

Notably, the aberrant transcripts isolated from lipomas with rearrangements of 6p21–23 were generated by internal deletions within the translocated HMGI(Y) allele. This observation suggests that in lipomas and related benign mesenchymal tumors, HMGI genes may contain internal deletions and other submicroscopic rearrangements undetectable by cytogenetic techniques. It is likely therefore that the contribution of the HMGI genes to tumorigenesis is more significant than predicted by karyotypic analysis.

Misexpression of HMGI genes in a Differentiated Cell Results in Tumorigenesis To understand the biological function of the HMGI proteins, it is important to analyze their expression profiles during both normal and pathological growth. Prominently, high levels of the HMGI expression are observed during mouse embryonic development in midgestation but it essentially dissappears closer to the end of pregnancy. Subsequently, no HMGI expression can be detected in any of the adult tissues. Lipomas are composed of mature adipocytes which, like other terminally differentiated cells, normally do not express HMGI proteins. However, transcriptionally active HMGI alleles are consistently found in solid mesenchymal tumors with rearrangements of 12q13–15 and 6p21–23. Rearrangements of 12q13–15 or 6p21–23 activate an HMGI allele normally silent in adult cells and the resulting misexpression of the HMGI protein in the context of a differentiated mesenchymal cell is a crucial step in tumor development. A notable feature of this mechanism stems from the observation that during mouse embryonigenesis, HMGI-C is expressed in the mesenchymal component of the developing organs and tissues (unpublished data). Tumorigenesis in this case results from the temporally inappropriate expression in an adult cell of a gene that is normally expressed during prenatal development in an embryonic cell of the same lineage. This is reminiscent of observations in B-cell leukemias where rearrangements of 8q24 chromosomal area activate c-myc expression in a precursor cell of B-lineage and result in neoplasia. Unlike the HMGI family members, however, the endogenous expression of c-myc is not restricted to embryogenesis and its inappropriate expression takes place at the same time in the life of the organism when it is normally expressed. Even more different is a situation in some of the T-cell acute lymphoid leukemias where the cause of neoplasia is ectopic expression in T-cell precursors of HOX11, normally expressed in the embryonic liver.

Distinct Molecular Pathways of Tumorigenesis Exist in Lipomas

The molecular analysis of the lipomas described above yields valuable information about the expression state of the non-rearranged HMGI alleles. Wildtype HMGI expression, normally associated with tumorigenesis, was readily detectable in lipomas ST88–08203 and ST91–198, where chromosomal rearrangements produced an apparently normal HMGI(Y) and a truncated HMGI-C proteins, respectively. In contrast, the non-rearranged HMGI allele was not expressed in tumors ST92–24269 and ST93–724, where the aberrant HMGI transcripts were predicted to encode fusion proteins consisting of the HMGI DNA-binding domains fused to putative transcriptional regulatory domains.

The above findings indicate that there are at least two distinct molecular pathways by which tumorigenesis in lipomas can proceed. When a chromosomal rearrangement produces a disrupted HMGI protein with no intrinsic transcriptional activity, tumor development is dependent upon subsequent activation of the non-rearranged allele. However, the requirement for wildtype HMGI expression can be circumvented when, as a result of a translocation, a transcriptional regulatory domain is juxtaposed to the HMGI AT-hooks. The unlikely alternative mechanism, in which the non-rearranged allele is activated by the fusion protein through a positive HMGI regulatory mechanism, would postulate that such autoregulatory function is inhibited in the presence of transcriptional regulatory domains. Therefore, we conclude that distinct rearrangements of a single gene can activate alternative molecular pathways of tumor pathogenesis.

Molecular analysis of HMGI rearrangements in multiple tumor samples can now be combined with the expression studies of both disrupted and non-rearranged alleles to produce a mechanistically coherent model of lipoma development (Figure not shown). Tumor development is initiated when the chromosomal rearrangement disrupt an HMGI allele and results in the HMGI misexpression in a differentiated mesenchymal cell. Deletion within 3' UTR is probably the minimal rearrangement necessary for tumor formation. Subsequently, one of the alternative tumorigenic pathways is selected based on the precise nature of the HMGI disruption. In the simplest model, the requirement for HMGI expression in tumorigenesis could be circumvented if HMGI DNA-binding domains are juxtaposed with a transcriptional regulatory domain (Figure not shown). The reduced number of events involved in tumor formation would readily explain the most frequently observed translocation in lipomas, t(3;12)(q29;q15), since it fuses DNA-binding domains of HMGI-C with LIM domains, motifs that are thought to function in transcriptional regulation.

The HMGI Proteins Play Different Roles in Tumors of Epithelial and Mesenchymal Origin Benign tumors, unlike their malignant counterparts, are characterized by a limited number of highly specific genetic alterations involving only a few chromosomal regions. It was proposed therefore that the molecular analysis of these neoplasms would identify genes of major importance for growth and proliferation. The above studies with HMGI(Y) and HMGI-C in lipomas demonstrate that misexpression of HMGI proteins plays a significant role in the development of a diverse array of human solid tumors. Clinically, a prominent feature of these benign mesenchymal tumors is the extremely low rate at which they convert to malignancy. Indeed, uterine leiomyomas progress to become leiomyosarcomas in less than 0.01% of the cases while conversion of lipoma to liposarcoma is even less frequent. Therefore, misexpression of HMGI proteins, while acting to increase the growth rate of the mesenchymal cells, does not seem to predispose the overproliferating cell to malignant transformation and may even play a protective role.

The apparent inability of the HMGI-expressing benign mesenchymal tumors to undergo malignant conversion is in a stark contrast with the situation seen in the tumors of epithelial origin. In these latter neoplasms, cellular hyperproliferation provides starting population for clonal expansion which, in turn, is followed by a stepwise progression to malignancy. Even more intriguingly, epithelial cells cannot be transformed by overexpression of HMGI-C while chromosomal rearrangements which could disrupt HMGI-C and HMGI(Y) are not found in tumors of the epithelial origin. Finally, in epithelial tumors activation of HMGI expression is associated with the advanced stages of carcinogenesis rather than with early hyperplasia. The asynchrony between the expression patterns of HMGI proteins in epithelial and mesenchymal cells as well as distinct phenotypes of the relevant tumors indicate that in tissues of different embryonic lineage HMGI proteins perform dissimilar functions.

One possible explanation for this phenomenon is provided by the fact that HMGI proteins normally function in the developing mesenchyma. The role of HMGI proteins in mesenchymal tumorigenesis may therefore be closely related to that during normal development, such as growth rate regulation. In the epithelial tumors, the HMGI architectural factors, expressed outside of their normal cellular milieu, may be recruited to take part in the transcriptional regulation of genes that are involved specifically in the final stages of tumor progression, such as invasion and metastasis. Regardless of the molecular details, the ability of HMGIC and HMGI(Y) to execute distinct functions during tumorigenesis in diverse cell types provides a powerful testimony to the biological potency of the HMGI proteins and accounts for the dramatic consequences of their disruption.

Translocation Breakpoints Upstream of the HMGI-C Gene in Uterine Leiomyomata

Translocation breakpoints in uterine leiomyomata reported here are in stark contrast to those observed in lipomas and other benign mesenchymal tumors in which translocations are found within the coding region of HMGI-C. Unlike the findings in uterine leiomyomata rearrangements in lipomas consistently result in disruption of HMGI-C, whereby DNA-binding A-T hook domains are separated from the 3' region of the gene. Because HMGI-C has no transcriptional activation domain (unpublished data), the pathobiology of lipomas appears to result from juxtaposition of direct or indirect activation domains with the DNA-binding A-T hook domains, although an alternative explanation of truncation of the protein cannot be ruled out at present.

These studies of uterine leiomyomata suggest a completely different molecular mechanism because the entire gene appears to be retained, suggesting that both the 5' DNA-binding domain and the 3' domain of unknown function are necessary. The finding that chromosomal rearrangements were located 10 to >100 kb upstream of HMGI-C in seven uterine leiomyomata suggests that breakpoints might disrupt regulatory elements and alter the normal expression of HMGI-C, analogous to Burkitt lymphoma, where translocations up to 100 kb upstream of MYC result in aberrant expression and neoplasia.

This "regulatory hypothesis" is supported by cytogenetic and FISH results for the karyotypically variant uterine leiomyoma ST89–171. In this tumor, three copies of HMGIC were present, suggesting a dosage mechanism for altered expression levels. Additionally, loss of the der(12) chromosome in ST89–171 provides further evidence that the der(14) chromosome, to which HMGI-C maps, contains the critical sequence.

This observation of an interstitial deletion upstream of HMGI-C in one uterine leiomyoma with a variant rearrangement of chromosome 12 is important for the cytogenetic and molecular interpretation of rearrangements in uterine leiomyomata and other tumors. This finding implies that uterine leiomyomata with unusual cytogenetic rearrangements of chromosome 12, and possibly other mesenchymal neoplasms without microscopically detectable chromosome 12 rearrangements, may have submicroscopic rearrangements of a critical region upstream of HMGI-C. Characterization of HMGI-C expression in uterine leiomyomata of all cytogenetic subgroups is now warranted for a more complete understanding of the pathobiologic mechanism.

Furthermore, this interpretation of a mechanism for dysregulation of HMGI-C in uterine leiomyomata is substantiated by observation of a rearrangement in a fibroid involving chromosomes 8 and 12 in which the 3' UTR of HMGI-C is disrupted. Such a rearrangement results similarly in retention of the entire coding region of HMGI-C, a finding previously noted in variant translocations in Burkitt lymphoma. However, this translocation breakpoint mapping in uterine leiomyomata and the deregulation model differ largely from that reported by others in which intragenic breakpoints were found for some fibroids perhaps reflecting the relatively limited number of tumors analyzed. Alternatively, although there are no data to support the existence of alternative 5' exons of HMGI-C or other uncharacteristic genes in the region, such possibilities, which might be affected by chromosomal rearrangement and contribute to tumor biology, cannot be excluded. Regardless, a mechanism of dysregulation not involving a fusion transcript must be considered for tumors without intragenic rearrangements of HMGI-C because irrefutable data implicate HMGI-C as the critical gene in benign mesenchymal tumors with rearrangements of 12q14–15.

These findings are consistent with accumulating evidence for a primary role of HMGI-C in normal growth and differentiation of a variety of tissues. Besides expression of fusion transcripts in lipomas and other benign mesenchymal tumors and in mesenchymal components of tissues in the developing mouse embryo, expression of HMGI-C is found only in cells after they become transformed and has been found to be necessary, but not sufficient, for transformation. These studies indicate that HMGI-C also may be deregulated through translocation in uterine leiomyomata without involvement of a fusion transcript.

The present invention is further illustrated by the following examples which are not intended to limit the effective scope of the claims. All parts and percentages in the examples and throughout the specification and claims are by weight of the final composition unless otherwise specified.

EXAMPLES

HMGI Proteins in Adipogenesis and Mesenchyme Differentiation

The GenBank accession numbers for the novel sequences in the chimeric transcripts from ST90–375 and ST93–724 are U28131 and U28132, respectively.

Isolation of YACs at the Human Pygmy Locus

Initially, conserved fragments were isolated from the cloned, mouse pygmy locus (Xiang et al., 1990; K. Benson and K. C., unpublished observations) and were used as probes on a normal, human lambda genomic library (Sambrook et al., 1989). The cross-hybridizing clones were isolated and relevant homologous fragments were subcloned and sequenced. Specific oligonucleotide primers (sequence 5'-AGGGGACAACAAATGCCCACAGG SEQ ID NO: 1 and 5'-CGTCACCAGGGACAGTTTCACTTGG SEQ ID NO: 2) were synthesized and used to screen a human total genomic YAC library by the PCR-based method (Green and Olson, 1990). Four positive clones of Saccharomyces cerevisiae containing YACs yWPR383, yWPR384, yWPR385 and yWPR386 were isolated.

Construction and Screening of Phage Libraries

High molecular weight DNA was isolated from yeast strains harboring YACs yWPR383 and yWPR384 (Guthrie and Fink, 1991), and partially digested with Sau3A. After partial fill-in of the Sau3A site, DNA was subcloned at the partially filled XhoI site of the predigested lambda FIXII vector (Stratagene, La Jolla, Calif.) and packaged in vitro (GIGAPACK II packaging extract, Stratagene). To select clones derived from the human YACs, 6000 plaques from each library were probed with total human genomic DNA and hybridizing plaques were spotted on plates inoculated with SRB(P2) cells in a gridded array. After incubating the plates at 39° C. for 12 hours, plaques were transferred onto DURALON (Stratagene) membranes. These grids were used for identifying lambda clones that contained human HMGI-C exons by probing with mouse HMGI-C cDNA (unpublished results), using the same hybridization conditions as detailed below for Southern analysis. Overlaps between contiguous clones and colinearity with the genome were confirmed by a combination of clone to clone and clone to genomic hybridizations along with restriction mapping.

Southern Blot Analysis

10–12 mg of human DNA was digested with the appropriate restriction enzymes, products resolved on 0.8% agarose gels and transferred onto DURALON (Stratagene) membranes. Blots were treated with prehybridization solution (50% formamide, 5× SSC, 10× Denhardt's solution, 0.05M sodium phosphate pH 6.8, 0.001M EDTA, 0.01 mg/ml denatured salmon sperm DNA, and 0.2% SDS) for 2 hours at 42° C. Probes were added to the hybridization solution (50% formamide, 5× SSC, 1× Denhardt's solution, 0.02M sodium phosphate pH 6.8, 0.001M EDTA, 0.01 mg/ml denatured salmon sperm DNA, 0.2% SDS and 10% dextran sulfate) and hybridization was performed for 16 hours at 42° C. Membranes were washed with 2× SSC, 0.001M EDTA, 0.5% SDS, 0.05% NaPPi and 0.01M sodium phosphate pH 6.8, at 65° C. for 3× 1 hour periods and exposed to X-ray film at −70° C. with intensifying screens.

Identification and Characterization of Chimeric Transcripts

First strand cDNA was synthesized in a 20 ml reaction using an anchored oligo-dT primer 5'-GCAATACGACTCACTATAG(T)$_{13}$ SEQ ID NO: 3 and Superscript II RT reverse transcriptase (BRL, Gaithersburg, Md.) according to the manufacturer's protocol. Primers used in the first round of 3' RACE (Ausubel et al., 1989) were an HMGI-C exon 1 sense primer 5'-CTTCAGCCCAGGGACAACC SEQ ID NO: 4 and an antisense adapter primer 5'-GCAATACGACTCACTATAG SEQ ID NO: 5. One ml of first-strand cDNA was combined with 25 pmole of sense primer in a 50 ml reaction mixture (60 mM Tris-SO$_4$ (pH 9.1 at 25° C.); 18 mM (NH$_4$)$_2$SO$_4$; 2 mM MgSO$_4$; each dNTP at 200 mM; 2.5 U of Taq DNA polymerase (BRL)), denatured for 2 minutes at 94° C. and subjected to 5 cycles of linear amplification (Rother, 1992) using the following conditions: 94° C., 30 seconds; 58° C., 20 seconds; 72° C., 1 minute 30 seconds. Ten pmole of antisense primer were then added and 25 cycles of exponential amplification were performed (94° C., 30 seconds; 56° C., 30 seconds; 72° C., 1 minute 30 seconds).

One ml of the PCR reaction was reamplified for 20 cycles with a nested HMGI-C sense primer spanning exon 1 and 2, 5'-GGAAGCAGCAGCAAGAACC SEQ ID NO: 6 as described above. Five ml of each reaction were analyzed on a 1.5% agarose gel. Reverse transcription for the detection of chimeric transcripts using novel sequence-specific primers was performed as above except primers 375 (5'-CTTCTTTCTCTGCCGCATCG SEQ ID NO: 7) for ST90–375 and 724 (5'-GTGAGGATGATAGGCCTTCC SEQ ID NO: 8) for ST93–724 were used. Subsequent PCR conditions were an initial denaturation at 94° C. for 2 minutes; 30 cycles at 94° C., 30 seconds; 58° C., 30 seconds; 72° C., 1 minute, followed by a final extension for 10 minutes at 72° C.

Chimeric transcripts amplified by 3'-RACE and RT-PCR were isolated from the gel, blunt-end cloned by standard methods (Sambrook et al., 1989) into the pCR-Script vector (Stratagene) and sequenced using the Sequenase kit Version 2.0 (USB, Cleveland, Ohio).

Chromosomal Localization of Novel Sequences

The NIGMS monochromosomal somatic cell hybrid mapping panel #2 was obtained from the Coriell Cell Repositories (Coriell Institute for Medical Research, Camden, N. J.). Primers used were derived from the novel sequences of the chimeric transcripts and 500 ng of genomic DNA from each somatic cell line was used as a template for PCR amplification. For the novel sequence derived from the chimeric transcript obtained from lipoma ST90–375, the primers were 5'-CAGAAGCAGACCAGCAAACC SEQ ID NO: 9 and 5'-CTTCTTTCTCTGCCGCATCG SEQ ID NO: 10 and from lipoma ST93–724, the primers were 5'-CTCTGGAGCAGTGCAATGTG SEQ ID NO: 11 and 5'-GTGAGGATGATAGGCCTTCC SEQ ID NO: 12. PCR conditions for the ST93–724 novel sequence primers were 26 cycles of 94° C., 15 seconds; 64° C., 30 seconds; 72° C., 1 minute. For ST90–375, the same conditions were used except that the annealing temperature was 62.5° C. PCR products were analyzed on a 7% acrylamide gel.

Tumor Cell Lines and Chromosome Preparations

Lipoma specimens were obtained from patients at the time of surgery. Tumor culture, metaphase chromosome harvesting, slide preparation, and trypsin-Giemsa banding were performed as described previously (Fletcher et al., 1991). Metaphases with rearrangements of chromosome 12 in band q15 were identified and corresponding cell pellets stored in fixative at −20° C. were used to prepare slides for FISH. These slides were stored at room temperature for at least 10 days prior to hybridization.

Lambda clones shown in FIG. 1 were mapped to lipoma tumor metaphase chromosomes from ST90–375[46,XX,t(12;15)(q15;q24)], ST91–198 [46,XX,t(12; 13)(q15;q21–32)], and ST93–724 [46,XX,t(3; 12)(q29;q15)] Karyotypes for lipomas ST90–375 and ST91–198 have been reported previously (Fletcher et al., 1993).

FISH with Lambda Clones

Slides for FISH were prepared as recommended in the Hybridization Kit (Oncor, Gaithersburg, Md.) except for denaturation at 68° C. for 30 seconds.

Lambda probes were labeled with digoxigenin-11-dUTP (Boehringer Mannheim, Indianapolis, Ind.) using 1 mg of the appropriate lambda DNA using dNTPs obtained from Boehringer Mannheim and the DNase I/DNA polymerase I mix from the BioNick Labeling System (BRL). Labeling reactions were performed at 16° C. for 2 hours. 500 ng of digoxigenin-labeled lambda probe was lyophilized with 5 mg of Cot-1 DNA (BRL) and resuspended in 20 ml deionized water. 2 ml of resuspended probe was added to 9 ml Hybrisol VI (Oncor). The lambda probe was denatured, hybridized to slides, and washed according to standard protocols (Oncor). Digoxigenin-labeled lambda clones were detected using the fluorescein-labeled antidigoxigenin antibody (Oncor) according to the manufacturer's recommendations. Metaphase chromosomes were counterstained with 4,6-diamidino-2-phenylindole-dihydrochloride (DAPI) according to the protocol supplied by Oncor. Hybridization was observed using a Zeiss Axioskop microscope and images captured with the CytoVision Imaging System (Applied Imaging).

FIGS. 1(A) and 1(B) illustrate the genomic structure of the human HMGI-C gene. FIG. 1(A): 403, H409, H5003, H1001 and H4002 are genomic lambda FIXII clones (see Materials and Methods) that contain the five exons (E1–E5) of the human HMGI-C gene. FIG. 1(B): Exons are denoted by boxes and introns by a line. Overlapping lambda clones were not obtained within intron 3 and this region is denoted with a dashed line. Sequences encoding potential functional domains, AUG and UAG codons are shown in the exons. The A-T hook motifs of the DNA-binding domains are shown as stippled areas and the solid region (in E5) encodes for the acidic domain of unknown function. The Figure is not drawn to scale because of the large 5' and 3' UTRs.

FIGS. 2(A) through 2(F) illustrate FISH mapping of HMGI-C lambda clones to lipoma tumor metaphase chromosomes from three lipomas revealing rearrangement of HMGI-C in all three tumors. The normal chromosome 12 homologs provide internal positive hybridization controls and are marked by yellow arrows in each metaphase, while derivative chromosomes are marked by red arrows. Lambda clones H403 and H409 from the 5' end of HMGI-C were used as FISH probes to lipoma metaphase chromosomes from FIG. 2(A) ST90–375 and FIG. 2(C) ST93–724, respectively. Note hybridization on the normal chromosome 12 and the der(12), demonstrating that these clones map proximal to the breakpoint in both lipomas. In contrast, when H403 was hybridized to lipoma metaphase chromosomes from FIG. 2(E) ST91–198, hybridization was observed on the der(13) showing a map position distal to the breakpoint in this tumor. H4002 from the 3' end of HMGI-C was used as a FISH probe to lipoma metaphase chromosomes from FIG. 2(B) ST90–375 and FIG. 2(D) ST93–724; note hybridization on the normal chromosome 12 and the der(15) or der(3), respectively, indicating that these clones map distal to the breakpoint in both lipomas. However, FISH with H4002 from the 3' end of HMGI-C on FIG. 2(F) ST91–198 revealed hybridization on the normal chromosome 12 only, suggesting this clone is deleted from either der (12) or der(15) in this tumor. Metaphase spreads were counterstained with DAPI. Lipoma karyotypes are: ST90–375, t(12;15)(q15;q24); ST93–724, t(3;12)(q29;q15); ST91–198, t(12;13) (q15;q21–32).

FIG. 3 illustrates RT-PCR amplification of HMGI-C chimeric transcripts. 3' RACE on RNA from lipomas ST90–375 (375) and ST93–724 (724) yield 441 bp and 672 bp products. Reverse transcription was performed with an oligo-dT primer linked to an adapter sequence and was followed by a nested PCR with sense primers from exon 1 and spanning exons 1 and 2. DLD-1 is a colorectal adenocarcinoma cell line that expresses wild-type HMGI-C (data not shown) but under these conditions, the predicted 3.1 kb wild-type message was not amplified. Products were analyzed on a 1.5% agarose gel. M are molecular weight markers in kilobases.

FIG. 4 illustrates rearrangements of 12q15 in human lipomas which disrupt the HMGI-C gene and produce chimeric transcripts. HMGI-C denotes the nucleotide and amino acid sequence of the wildtype gene and the open box sequence corresponds to the end of HMGI-C exon 3. t(3;12) and t(12;15) refer to the nucleotide and predicted amino acid sequences of the chimeric transcripts from the cloned cDNA products obtained by 3' RACE on RNA isolated from primary cell cultures of ST93–724, t(3;12), and ST90–375, t(12;15), respectively. Chr. 3 and Chr. 15 refer to the novel sequences derived from chromosome 3 or 15 in t(3;12) and t(12;15) lipomas, respectively. Only the sequences immediately adjacent to the fusion sites are shown.

FIG. 5 illustrates RT-PCR using primers located on either side of the fusion site between HMGI-C and novel sequences. RNA refers to the lipoma source of total RNA. Primer 375 is an oligonucleotide that is complementary to the novel sequence from the chimeric transcript of lipoma ST90–375 and is located 8 nucleotides downstream of the fusion point. Primer 724 is a complementary oligonucleotide to the novel sequence from the chimeric transcript of lipoma ST93–724 and is located 425 nucleotides downstream of the fusion point. Total RNA from both lipoma primary cell cultures was reverse transcribed using either 375 or 724 primers and PCR amplified using HMGI-C sense primer (which spans exons 1 and 2) and the antisense primer used for reverse transcription. Expected product sizes are: 180 bp from ST90–375 cDNA with 375 primer and 597 bp from ST93–724 cDNA with 724 primer.

FIGS. 6(A) and 6(B) illustrate novel sequences fused to the DNA binding-domains of HMGI-C which encode transcriptional regulatory domains.

FIG. 6(A) illustrates a comparison of the novel chromosome 3 sequence from ST93–724 with the LIM domain-containing proteins, zyxin (Sadler et al., 1992), apterous (ap) (Cohen et al., 1992), Lh2 (Xu et al., 1993), Lin11 (Freyd et al., 1990), RBTN-1 (McGuire et al., 1989). Amino acids that constitute the LIM domain consensus are highlighted. The amino acid spacing between the consensus residues is indicated by an x. In addition to the totally conserved cysteine, histidine and aspartic acid residues (Sadler et al., 1992), LIM domains are characterized by the presence of an aromatic residue adjacent to the first histidine and a leucine located C-terminal to the central HxxCxxCxxC cluster. The positions of these conserved residues are indicated by arrows. Each LIM domain is designated 1, 2 or 3 depending on its position relative to the N-terminus. The uninterrupted sequence of the two LIM domains in the various proteins are shown and gaps were introduced to permit alignment of the two LIM domains.

FIG. 6(B) illustrates the potential transactivation acidic domain encoded by the sequence derived from chromosome 15 in ST90–375. Acidic residues are underlined and the amino acids, serine and threonine, are in bold type.

FIG. 7 illustrates the structure and domain organization of HMGI-C and the predicted fusion proteins. The vertical dashed line shows the location of junction sites in the chimeric products. DNA binding domains of HMGI-C (AT) are preserved in the fusion proteins but the C-terminal domain (stippled) is replaced by potential transcriptional regulatory domains. LIM, LIM domain; (—), acidic domain; S,T, serine-threonine rich domain.

HMGI Proteins in Mammalian Growth and Development

Figure 8:
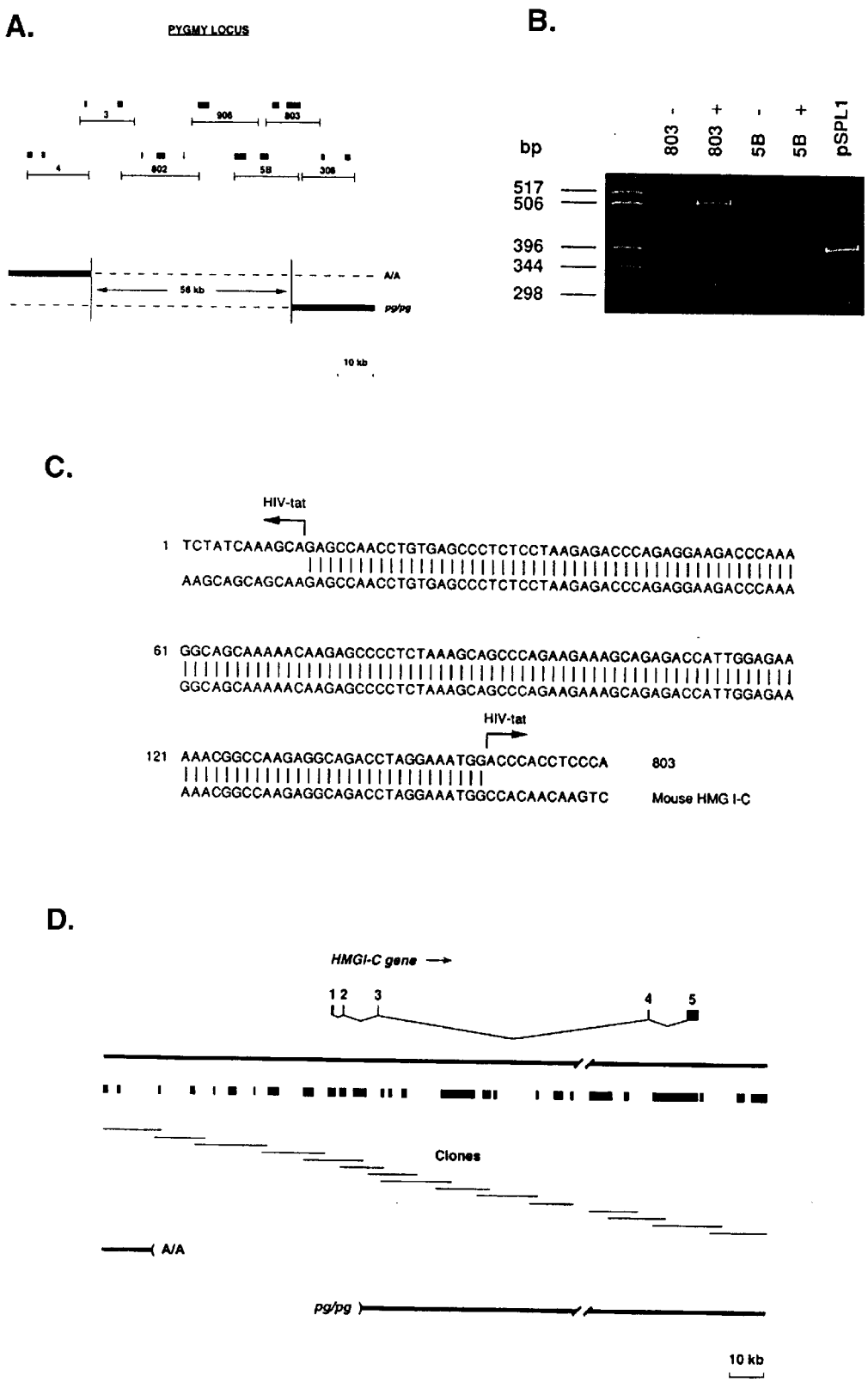
FIGS. 8(A) through (D) illustrate the identification and genomic characterization of the HMGI-C gene at the pygmy locus in normal and mutant alleles.

FIGS. 8(A) through (D) illustrate the identification and genomic characterization of the HMGI-C gene at the pygmy locus in normal and mutant alleles. FIG. 8(A): Delineation of the overlapping deleted genomic regions at the pygmy locus in the spontaneous and transgenic insertional mouse mutants. The open box above clone 3 positions the 0.5 kb ApaI—ApaI fragment and the filled boxes represent single copy sequences used as probes to analyze genomic DNA isolated from mice of varying genotypes (Xiang, X. et al., 1990). Solid and dashed lines represent presence or absence of genomic sequences, respectively, in the transgenic insertional mouse mutant pg$^{TgN40ACha}$ (A) and the spontaneous mutant pygmy (pg). FIG. 8(B): Exon amplification from lambda clones 803 and 5B. The primary PCR exon amplification products in both sense (+) and antisense (−) orientations from the lambda clones shown in FIG. 8(A) were analyzed on a 5% polyacrylamide gel (Buckler, A. et al., 1991). The 379 bp PCR product observed in the control pSPL1 lane results from splicing between the HIV tat and b-globin vector sequences (Buckler, A. et al., 1991). FIG. 8(C): Sequence of exons amplified from clone 803 and comparison to the HMGI-C gene. FIG. 8(D): A series of overlapping phage clones extending approximately 190 kb at the pygmy locus. The discontinuous region represents an unclonable 11 kb fragment as estimated from Southern blots of cleaved genomic DNA probed with single copy sequences from the end of the clonable region. The position and number of the HMGI-C exons (not drawn to scale) are shown above the wildtype locus. Single copy sequences were isolated at the indicated positions and are represented by filled boxes below the wildtype locus. Thick bars and blank regions represent the genomic sequences that are present or deleted in the two alleles.

Methods. The 0.5 kb ApaI—ApaI fragment (Xiang, X. et al., 1990) was used as a probe to isolate clones 3 and 4 from an EMBL3 mouse genomic library (a kind gift of Dr. E. Lacy) and a YAC (902CO711) from a mouse YAC library (Lehrach, H. et al., 1990). YAC 902CO711 was further subcloned into lambda FIX II (Ausubel, F. et al., 1988) and 86 clones that hybridized to radioactively-labeled mouse genomic DNA were picked and transferred to new plates in a gridded array (Ausubel, F. et al., 1988). Lambda clones 802, 906, 5B, 803 and 308 were isolated after the walk was initiated with the 0.5 kb ApaI—ApaI fragment and accomplished by repeated hybridization to filters of the array. Overlaps between the contig clones and colinearity with the genome were confirmed by a combination of clone to clone and clone to genomic hybridizations along with restriction mapping. Exon amplification was performed (Exon Trapping System, Gibco BRL) after the genomic inserts from the lambda clones were removed by cleavage with SalI, partially filled-in (Ausubel, F. et al., 1988) and subcloned into a partially filled-in BaniHl cleaved pSPL1 plasmid (Buckler, A. et al., 1991). The DNA was electroporated into COS-7 cells at 180V and 960mF in a Bio-Rad Gene Pulser. Cytoplasmic RNA was isolated after 2–3 days and RT-PCR performed using primers supplied by the manufacturer. The secondary PCR amplification products (Buckler, A. et al., 1991) from clones 803 and 5B were subcloned into the plasmid vector, pAMP10 (Exon Trapping System, Gibco BRL) and sequenced using the Sequenase Version 2.0 sequencing kit (USB) (Ausubel, F. et al., 1988). A 344 bp fragment corresponding to the complete open reading frame of the HMGI-C gene (Manfioletti, G. et al., 1991) was amplified from 12.5 dpc mouse embryos (see text) using reverse transcription (RT) and PCR. Lambda clones containing the HMGI-C exons were then isolated by hybridization of the 344 bp radioactively-labeled fragment to the gridded array of lambda clones and subsequently connected through chromosome walking. The RT-PCR conditions for isolation of the 344 bp fragment consisted of first strand cDNA synthesis with primer 1 (5'-ATGAATTCCTAATCCTCCTCTGC-3'SEQ ID NO: 14), followed by PCR amplification with primers 1 and 2 (5'-ATGGATCCATGAGCGCACGCGGT-3'SEQ ID NO: 14). PCR conditions were 94° C., 0.5 minute; 55° C., 0.5 minute; 72° C., 1 minute; for 30 cycles. The amplified product was confirmed by sequencing analysis (Ausubel, F. etal., 1988).

FIG. 9 illustrates HMGI-C gene expression of three alleles at the mouse pygmy locus. The wildtype allele is represented by +, the transgenic allele pg$^{TgN40ACha}$ by A, the spontaneous mutant allele by pg and an allele at the pygmy locus which involves a paracentric inversion on chromosome 10 (In(10)17Rk) by Rk.

Methods. The genotypes were established for mice in line A and the spontaneous mutant pg as previously described (Xiang, X. et al., 1990), while mice containing the In(10) 17Rk inversion were detected by a PCR-based RFLP (unpublished results). RNA was isolated from 12.5 dpc embryos and equal amounts (5 mg) were analyzed by Northern blot hybridization (Ausubel, F. et al., 1988). The probes were a 138 bp nucleotide cDNA fragment encompassing exons 2 and 3 of the HMGI-C gene and a 340 bp cDNA fragment containing the complete coding sequence of the HMGI(Y) gene (Johnson, K. et al, 1988). The blot was subsequently hybridized to an oligonucleotide complementary to murine 28S ribosomal RNA (Barbu, V. & Dautry, F., 1989) to ensure equal amounts of RNA were present in each lane and the results are shown in the lower panel.

FIGS. 10(A) through(C) illustrate targeted disruption of the HMGI-C gene. FIG. 10(A): Targeting strategy. Endogenous HMGI-C gene (top), targeting vector (middle) and predicted mutant gene (bottom). The targeting vector was created by replacing the 3 kb DNA fragment containing exonl (E1) and exon2 (E2) with a PGK-neo cassette. The vector also includes a MC1-tk cassette at the 5' end of the long homologous segment. B, BamHI; Probe, a 4 kb HincII fragment used to identify the disrupted allele. FIG. 10(B): Southern blot analysis of mice from a heterozygous cross. DNA from tails of the mice was digested with BamHI and hybridized to the external probe (see FIG. 10(A)). The positions of the bands corresponding to the wildtype allele (10.5 kb) and the mutant allele (9.3 kb) are indicated. FIG. 10(C): Western blot analysis of wildtype (+/+), heterozygous (+/−) and homozygous (−/−) 12.5 dpc embryos with anti-GST-HMGIC rabbit IgG.

Methods. Genomic clones of the mouse HMGI-C gene were isolated from the mouse pygmy locus as described in FIG. 8 legend. Linearized vector (10 mg) was electroporated into AB1 ES cells at 280V, 500 mF, and homologous recombination events enriched for by selection with G418 (350 mg/ml) and 2 mM gangcyclovir (Syntex) on SNL76/7 feeder cells. Six targeted clones were obtained and three were injected into C57BL/6J blastocysts to generate chimaeras. Chimaeric males were mated to C57BL/6J females, and heterozygous offspring intercrossed to produce subsequent generations. Southern blot analysis of the progeny from heterozygous crosses was performed as described (Ausubel, F. et al., 1988) Proteins were extracted from 12.5 dpc mouse embryos from a heterozygous cross with lysis buffer containing 50 mM Tris-HCl (pH 7.5), 10% glycerol, 5 mM magnesium acetate, 0.2 mM EDTA, 1.0 mM PMSF, and 1% SDS. 10 mg of each sample was separated by 15% SDS-PAGE, transferred to a nylon membrane (Duralon, Stratagene) and HMGI-C was detected using rabbit IgG antimouse GST-HMGI-C, HRP-conjugated goat anti-rabbit IgG and ECL substrate (Amersham).

FIGS. 11(A) through (C) illustrate expression of HMGI-C in development and growth. FIG. 11(A): Temporal expression pattern of HMGI-C and HMGI(Y) determined by Northern blot analysis of RNA (5 mg) isolated from the head (H) and body (B) of mouse embryos whose ages in days post coitum are indicated at the top of the panel. No expression of HMGI-C was detected in placenta at any of these stages (data not shown). The probes are described in the legend of FIG. 9. FIG. 11(B): Spatial localization of HMGI-C transcripts in 11.5 dpc mouse embryos. Photomicrographs of 8 mm, adjacent, parasaggital sections through 11.5 dpc mouse embryos hybridized with the antisense (A) or sense (B) strand of exon 2 and 3 of HMGI-C or stained histochemically with haematoxylin and eosin (C). G, gut mesenchyme; H, heart; L, liver; Lb, limb bud; M, mandible; N, median nasal process; NE, neural epithelium; 0, otocyst. Magnification: 25X. FIG. 11(C): Growth of wildtype and pygmy embryonic fibroblasts. Fibroblasts derived from 13.5 dpc embryos were seeded at a concentration of $1.7 \times 10^3$ cells per cm2 in DMEM containing 10% fetal bovine serum. Cell number (ordinate) was determined on day 4. Small bars represent standard deviations of triplicate experiments. $P<0.001$. The genotypes of embryos were determined as previously described (Xiang, X. et al, 1990)

Methods. For in situ hybridization, CBA/J embryos (11.5 dpc) were fixed in 4% paraformaldehyde, dehydrated and embedded in paraffin. Paraffin sections were deparaffinized and hybridized with sense and antisense riboprobes corresponding to exons 2 and 3 of HMGI-C as previously described (Duncan, M. et al., 1992). Sections were stained with haematoxylin and eosin according to standard procedures.

Translocation Breakpoints Upstream of the HMGI-C Gene in Uterine Leiomyomata

Fluorescence in situ Hybridization (FISH)

Slides for FISH were prepared as recommended in the Hybridization Kit (Oncor, Gaithersburg, Md.), except for denaturation at 68° C. for 30 seconds.

HMGI-C clones were in the lambda FIXII vector (Stratagene, La Jolla, Calif.). They were labeled with digoxigenin-1-dUTP (Boehringer Mannheim, Indianapolis, Ind.) with 1 μg of the appropriate lambda DNA, dNTPs from Boehringer Mannheim, and the DNaseI/DNA polymerase mix from the BioNick Labeling System (BRL, Gaithersburg, Md.). Labeling reactions were performed at 16° C. for 2 hours. Five hundred nanograms of digoxigenin-labeled probe were lyophilized with 5 μg of Cot-1 DNA (BRL) and resuspended in 20 μl of deionized water. Two microliters of resuspended probe were added to 9 μl Hybrisol VI (Oncor). The probe was denatured, hybridized to slides, and washed according to standard protocols (Oncor). Digoxigenin-labeled lambda-clones were detected with fluorescein-labeled antidigoxigenin antibody (Oncor) according to the manufacturer's recommendations, and metaphase chromosomes were counterstained with 4,6diamidino-2-phenylindole-dihydrochloride (DAPI). Hybridization was observed with a Zeiss Axioskop microscope, and images were captured with the CytoVision Imaging System (Applied Imaging, Pittsburgh, Pa.)

Throughout this application, various publications have been referenced. The disclosures in these publications are incorporated herein by reference in order to more fully describe the state of the art.

REFERENCES

Aaronson, S. A. (1991), Science 254, 1146–1152.

Asher, H. R., Fejzo M. S., Tkachenko, A., Zhou, X., Fletcher, J. A., Weremowicz, S., Morton, C. C., and Chada, K., Cell 82 57–65 (1995)

Ausubel, F. M., Brent, R., Kingston, R. E., Moore, D. D., Seidman, J. G., Smith, J. A., and Struhl, K. (1989), Current Protocols in Molecular Biology (New York: Greene Publishing Associates and Wiley Interscience).

Barbu, V. & Dautry, F. Nucleic Acids Res. 17, 7115 (1989).

Benson, K. and Chada, K. (1994), Genet. Res. 64, 27–33.

Berlingieri, M. T., Manfioletti, G., Santoro, M., Bandiera, A., Visconti, R., Giancotti, V., and Fusco, A. (1995), Mol. Cell. Biol. 15, 1545–1553.

Bridge, J. A., Persons, D. L., Neff, J. R., and Bhatia, P. (1992), Cancer Detect. Prev. 16, 215–219.

Bridge, J. A., DeBoer, J., Walker, C. W., and Neff, J. R. (1995), Genes Chrom. Cancer 12, 70–72.

Buckler, A. et al. Proc. natn. Acad. Sci. U.S.A. 88, 4005–4009 (1991).

Bullerdiek, J., Wobst, G., Meyer-Bolte, K., Chilla, R., Haubrich, J., Thode, B., and Barnitzke, S. (1993), Cancer Genet. Cytogenet. 65, 27–31.

Chirgwin, J., Przybyla, A., MacDonald, R., and Rutter, W. J. (1979), Biochemistry 18, 5294–5299.

Cohen, B., McGuffin, M. E., Pfeifle, C., Segal, D., and Cohen, S. M. (1992), Genes Dev. 6, 715–729.

Dal Cin, P., Kools, P., De Jonge, I., Moerman, P., Van de Ven, W., and Van den Berghe, H. (1993), Genes Chrom. Cancer 8, 131–133.

de Thé, H., Lavau, C., Marchio, A., Chomienne, C., Degos, L., and Dejean, A. (1991), Cell 66, 675–684.

Du, W., Thanos, D., and Maniatis, T. (1993), Cell 74, 887–898.

Duncan, M., DiCicco-Bloom, E. M., Xiang, X., Benezra, R. & Chada, K. Dev. Biol. 154, 1–10 (1992).

Feuerstein, R., Wang, X., Song, D., Cooke, N. C., and Liebhaber, S. A. (1994), Proc. Natl. Acad. Sci. USA 91, 10655–10659.

Fletcher, J. A., Kozakewich, H. P., Hoffer, F. A., Lage, J. M., Weidner, N., Tepper, R., Pinkus, G. S., Morton, C. C., and Corson, J. M. (1991), N. Engl. J. Med. 324, 436–443.

Fletcher, J. A., Pinkus, G. S., Donovan, K., Naeem, T., Sugarbaker, D. J., Mentzer, S., Pinkus, J. L., and Longtine, J. (1992), Cancer Res. 52, 6224–6228.

Fletcher, J. A., Kozakewich, H. P., Schoenberg, M. L., and Morton, C. C. (1993), Genes, Chrom. Cancer 6, 24–29.

Fletcher, J. A., Longtine, J., Wallace, K., Mentzer, S. J., and Sugarbaker, D. J. (1995), Genes Chrom. Cancer 12, 210–223.

Freyd, G., Kim, S. K., and Horvitz, H. R. (1990), Nature 344, 876–879.

Friedmann, M., Holth, L. T., Zoghbi, H. Y., and Reeves, R. (1993), Nucleic Acids Res. 21, 4259–4267.

Frohman, M. A., Dush, M. K., and Martin, G. R. (1988), Proc. Natl. Acad. Sci. USA 85, 8998–9002.

German, M. S., Wang, J., Chadwick, R. B., and Rutter, W. J. (1992), Genes Dev. 6, 2165–2176.

Giancotti, V., Pani, B., Andrea, P. D., Berlingieri, M. T., Di Fiore, P. P., Fusco, A., Vecchio, G., Philp, R., Crane-Robinson, C., Nicolas, R. H., Wright C. A., and Goodwin, G. H. (1987), EMBO J. 6, 1981–1987.

Giancotti, V., Buratti, E., Perissin, L., Zorzet, S., Balmain, A., Portella, G., Fusco, A., and Goodwin, G. H. (1989), Exp. Cell Res. 184, 538–545.

Giancotti, V., Bandiera, A., Ciani, L., Santoro, D., Crane-Robinson, C., Goodwin, G. H., Boiocchi, M., Dolcetti, R., and Casetta, B. (1993), Eur. J. Biochem. 213, 825–832.

Green, E. D. and Olson, M. V. (1990), Proc. Natl. Acad. Sci. USA 87, 1213–1217.

Green, M. C. in Genetic Variants and Strains of the Laboratory Mouse (eds. Lyon, M. & Searle, A.) 12–403 (Oxford University Press, Oxford, 1989).

Grosschedl, R., Giese, K. and Pagel, J. (1994), Trends Gen. 10, 94–100.

Gu, Y., Nakamura, T., Alder, H., Prasad, R., Canaani, O., Cimino, G., Croce, C. M., and Canaani, E. (1992), Cell 71, 701–708.

Guthrie, C. and Fink, G. R. (1991), Meth. Enzymol. 194, 218–219.

Hatano, M., Roberts, C. W. M., Minden, M., Crist, W. M., and Korsmeyer, S. J. (1991), Science 253, 79–82.

Hirabayashi, Y., Yoshida, M. A., Ikeuchi, T., Ishida, T., Kojima, T., Higaki, S., Machinami, R., and Tonomura, A. (1992), Cancer Genet. Cytogenet. 60, 35–40.

Jenkins, R. B., Kimmell, D. W., Moertel, C. A., Schultz, C. A., Menezes, R. M., Scheihauer, B., Kelly, P. J., and Dewald, G. W. (1989), Cytogenet. Cell Genet. 51, 1019.

Johnson. K. R., Lehen, D. A., Elton, T., Barr, P., and Reeves, R. (1988), J. Biol. Chem. 263, 18338–18342.

Johnson, K. R., Lehen, D. A., and Reeves, R. (1989), Mol. Cell. Biol. 9, 2114–2123.

Justice, M. J., Siracusa, L. D., Gilbert, D. J., Heisterkamp, N., Groffen, J., Chada, K., Silan, C., Copeland, N. and Jenkins, N. A. (1990), Genetics 125, 855–866.

Kamps, M. P., Look, A. T., and Baltimore, D. (1991), Genes Dev. 5, 358–368.

Karlsson, O., Thor, S., Norbert, T., Ohlsson, H., and Edlund, T. (1990), Nature 344, 879–882.

King, J. *Genetics* 53, 487–497 (1955).

Lehrach, H. et al. in *Genome Analysis Volume* 1: *Genetic and Physical Mapping* (eds Davies, K. & Tilghman, S.) 39–81 (Cold Spring Harbor Laboratory Press, New York, 1990).

Li, S. et al. *Nature* 347, 528–533 (1990).

Lin, S -C. et al. *Nature* 364, 208–213 (1993).

Ma, Q., Alder, H., Nelson, K. K., Chatterjee, D., Gu, Y., Nakamura, T., Canaani, E., Croce, C. M., Siracusa, L. D., and Buchberg, A. M. (1993), Proc. Nati. Acad. Sci. USA 90, 6350–6354.

MacArthur, J. (1944), Amer. Nat. 78, 142–157.

Mandahl, N., Heim, S., Arheden, K., Rydholm, A., Willen, H., and Mitelman, F. (1988), Hum. Genet. 79, 203–208.

Mandahl, N., Heim, S., Arheden, K., Rydholm, A., Willen, H., and Mitelman, F. (1989), Cancer 65, 242–248.

Mandahl, N., Omdal, C., Heim, S., Willen, H., Rydholm, A., Bauer, H. C. F., and Mitelman, F. (1993a), Cancer 71, 3009–3013.

Mandahl, N., Willen, H., Rydholm, A., and Mitelman, F. (1993b), Genes Chrom. Cancer 6, 121–123.

Manfioletti, G., Giancotti, V., Bandiera, A., Buratti, E., Sautiere, P., Cary, P., Crane-Robinson, C., Coles, B., and Goodwin, G. H. (1991), Nucleic Acids Res. 19, 6793–6797.

May, W. A., Gishizky, M. I., Lessnick, S. L., Lunsford, L. B., Lewis, B. C., Delattre, O., Zucman, J., Thomas, G., and Denny, T. D. (1993), Proc. Natl. Acad. Sci. USA 90, 5752–5756.

McGuire, E. A., Hockett, R. D., Pollock, K. M., Bartholdi, M. F., O'Brien, S. J., and Korsmeyer, S. J. (1989), Mol. Cell. Biol. 9, 2124–2132.

Mitchell, P. J., and Tijan, R. (1989), Science 245, 371–378.

Nilbert, M., and Heim, S. (1990), Genes Chrom. Cancer 2, 3–13.

Nissley, S., Knazek, R. & Wolff, G. *Horm. Metab. Res.* 12, 158–164 (1980).

Noguera, R., Llombart-Bosch, A., Lopez-Gines, C., Carda, C., and Fernandez, C. (1989), Virchows Arch. A. Pathol. Anat. Histopathol. 415, 377–382.

Patel, U. A., Bandeira, A., Manfioletti, G., Giancotti, V., Chau, K -Y., and Crane-Robinson, C. (1994), Biochem. Biophys. Res. Comm. 201, 6370.

Pendergast, A. M., Muller, A. J., Havlik, M. H., Maru, V., and Witte, O. N. (1991), Cell 66, 161–171.

Prasad, R., Leshkowitz, D., Gu, Y., Alder, H., Nakamura, T., Saito, H., Huebner, K., Berger, R., Croce, C. M., and Canaani, E. (1994), Proc. Natl. Acad. Sci. USA 91, 8107–8111.

Rabbitts, T. H. (1994), Nature 372, 143–149.

Ram, T., Reeves, R. & Hosick, H. L. *Cancer Res.* 53, 2655–2660 (1993).

Reeves, R., and Nissen, M. S. (1990), J. Biol. Chem. 265, 8573–8582.

Reeves, R., Langan, T. A. & Nissen, M. S. *Proc. natn. Acad. Sci. U.S.A.* 88, 4005–4009 (1991).

Rein, M. S., Friedman, A. J., Barbieri, R. L., Pavelka, K., Fletcher, J. A., and Morton C. C. (1991), Obstet. Gynecol. 77, 923–926.

Rogers, P., and Webb, G. P. (1980), British J. Nutrition 43, 83–86.

Rohen, C., Bonk, U., Staats, B., Bamitzke, S., and Bullerdiek, J. (1993), Cancer Genet. Cytogenet. 69: 68–71.

Rother, R. P. (1992), Biotechniques 13, 524.

Sadler, I., Crawford, A. W., Michelsen, J. W., and Beckerle, M. C. (1992), J. Cell Biol. 119, 1573–1587.

Saitoh, Y. & Laemmli, U. K. *Cell* 76, 609–622 (1994).

Sambrook, J., Fritsch, E. F. and Maniatis, T. (1989). Molecular cloning: A Laboratory Manual, 2nd edition (Cold Spring Harbor, N.Y.: Cold Spring Harbor Laboratory Press).

Sánchez-Garcia, I., Osada, H., Forster, A., and Rabbitts, T. H. (1993), EMBO J. 12, 4243–4250.

Sánchez-Garcia, I., and Rabbitts, T. H. (1993), Sem. Cancer Biol. 4, 349–358.

Sandros, J., Stenman, G., and Mark, J. (1990), Cancer Genet. Cytogenet. 44, 153–167.

Schmitz, M. L., and Baeuerle, P. A. (1991), EMBO J. 10, 3805–3817.

Schoenberg Fejzo, M., Yoon, S -J, Montogomery, K., Rein, M. S., Weremowicz, S., Krauter, K. S., Dorman, T. E., Fletcher, J. A., Mao, J., Moir, D. T., Kucherlapati, R. S. and Morton, C. C. (1995), Genomics 26, 265–271.

Seipel, K., Georgiev, O., and Schaffner, W. (1992), EMBO J. 11, 4961–4968.

Sinha, Y., Wolff, G., Baxter, S. & Domon, O. *Proc. Soc. Expt. Biol. Med.* 162, 221–223 (1979).

Sreekantaiah, C., Leong, S. P. L., Karakousis, C. P., McGee, D. L., Rappaport, W. D., Villar, H. V., Neal, D., Fleming, S., Wankel, A., Herrington, P. N., Carmona, R., and Sandberg, A. (1991), Cancer Res. 51, 422–433.

Thanos, D., and Maniatis, T. (1992), Cell 71, 777–789.

Tjian, R. & Maniatis, T. *Cell* 77, 5–8 (1994).

Tkachuk, D. C., Kohler, S., and Cleary, M. L. (1992), Cell 71, 691–700.

Valge-Archer, V. E., Osada, H., Warren, A. J., Forster, A., Li, J., Baer, R., and Rabbitts, T. H. (1994), Proc. Natl. Acad. Sci. USA 91, 86172–86212.

Vanni, R., Dal Cin, P., Marras, S., Moerman, P., Andria, M., Valdes, E., Deprest, J., and Van den Berghe, H. (1993), Cancer Genet. Cytogenet. 68, 32–33.

Vartainen, E., Palvimo, J., Mahonen, A., Linnala-Kankkunen, A., and Maenpaa P. H. (1988), FEBS Lett. 228, 45–48.

Way, J. C., and Chalfie, M. (1988), Cell 54, 5–16.

Wolffe, A. (1994), Science 264, 1100–1101.

Xiang, X., Benson K. F., and Chada, K. (1990), Science 247, 967–969.

Xu, Y., Baldassare, M., Fisher, P., Rathbun, G., Oltz, E. M., Yancopoulos, F. W. (1993), Proc. Natl. Acad. Sci. USA 90, 227–231.

Zhou, X., Benson, K. F., Ashar, H. R., and Chada, K., Nature 376 771–774 (1995).

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A method for detecting high mobility group DNA-binding proteins (HMGI-C) as a diagnostic marker for benign mesenchymal or lipoma rumors using a probe for a sample, or an extract of the sample, from a patient that recognizes HMGI-C, which comprises the steps of:
   (a) contacting HMGI-C from a sample from a patient with a probe which binds to HMGI-C; and
   (b) analyzing for HMGI-C by detecting levels of the probe bound to the HMGI-C;
   (c) treating a control sample according to the method to assess the level of HMGI-C in the control sample;
wherein the presence of HMGI-C in the sample in step (b) in an amount higher than the amount in the control sample in step (c) is diagnostic for a benign mesenchymal or lipoma tumor.

2. The method according to claim 1, wherein the sanple is selected from the group consisting of a biopsy sample, a urine sample, a blood sample, a feces sample, and a saliva sample.

3. The method according to claim 1, wherein the method is selected from the group consisting of a histological assay, biochemical assay, flow cytometry assay, Western blot assay, and capture assay.

4. A methdod for detecting high mobility group DNA-binding proteins (HMGI-Y) as a diagnostic marker for a benign mesenchymal tumor using a probe for a sample, or an extract of the sample, from a patient that recognizes HMGI-Y, which comprises the steps of:
   (a) contacting HMGI-Y from a sample from a patient with a probe which binds to HMGI-Y; and
   (b) analyzing for HMGI-Y by detecting levels of the probe bound to the HMGI-Y;
   (c) treating a control sample according to the method to assess the level of HMGI-Y in the control sample;
wherein the presence of HMGI-Y in the sample in step (b) in an amount higher than the amount in the control sample in step (c) is diagnostic for a benign mesenchymal tumor.

5. The method according to claim 4, wherein the sample is selected from the group consisting of a biopsy sample, a urine sample, a blood sample, a feces sample, and a saliva sample.

6. The method according to claim 4, wherein the method is selected from the group consisting of a histological assay, biochemical assay, flow cytometry assay, Western blot assay, and capture assay.

7. A method for detecting high mobility group DNA-binding proteins (HMGI-C or HMGI(Y)) as a diagnostic marker for malignant tumors using a probe for a sample, or an extract of the sample, from a patient that recognizes HMGI-C or HMGI(Y), which comprises the steps of:
   (a) contacting HMGI-C or HMGI(Y) from a sample from a patient with a probe which binds to HMGI-C or HMGI(Y), respectively; and
   (b) analyzing for HMGI-C or HMGI(Y) by detecting levels of the probe bound to the HMGI-C or HMGI(Y), respectively;
   (c) treating a control sample according to the method to assess the level of HMGI-C or HMGI(Y) in the control sample;
wherein the presence of HMGI-C or HMGI(Y) in the sample in step (b) in an amount higher than the amount in the control sample in step (c) is diagnostic for a malignant tumor.

8. The method according to claim 7, wherein the sample is selected from the group consisting of a biopsy sample, a urine sample, a blood sample, a feces sample, and a saliva sample.

9. The method according to claim 7, wherein the method is selected from the group consisting of a histological assay, biochemical assay, flow cytometry assay, Western blot assay, and capture assay.

\* \* \* \* \*

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 23 base pairs
       (B) TYPE: nucleic acid
       (C) STRANDEDNESS: unknown
       (D) TOPOLOGY: unknown (ii) MOLECULE TYPE: DNA (genomic)

(iii) HYPOTHETICAL: NO (xi) SEQUENCE DESCRIPTION: SEQ ID NO:1:

AGGGGACAAC AAATGCCCAC AGG                                              23

(2) INFORMATION FOR SEQ ID NO:2:

(i) SEQUENCE CHARACTERISTICS:
       (A) LENGTH: 25 base pairs
       (B) TYPE: nucleic acid
       (C) STRANDEDNESS: unknown
       (D) TOPOLOGY: unknown (ii) MOLECULE TYPE: DNA (genomic)

(iii) HYPOTHETICAL: NO (xi) SEQUENCE DESCRIPTION: SEQ ID NO:2:

CGTCACCAGG GACAGTTTCA CTTGG                                            25

(2) INFORMATION FOR SEQ ID NO:3:

(i) SEQUENCE CHARACTERISTICS:
       (A) LENGTH: 32 base pairs
       (B) TYPE: nucleic acid
       (C) STRANDEDNESS: unknown
       (D) TOPOLOGY: unknown (ii) MOLECULE TYPE: DNA (genomic)

(iii) HYPOTHETICAL: NO (xi) SEQUENCE DESCRIPTION: SEQ ID NO:3:

GCAATACGAC TCACTATAGT TTTTTTTTTT TT                                    32

(2) INFORMATION FOR SEQ ID NO:4:

(i) SEQUENCE CHARACTERISTICS:
       (A) LENGTH: 19 base pairs
       (B) TYPE: nucleic acid
       (C) STRANDEDNESS: unknown
       (D) TOPOLOGY: unknown (ii) MOLECULE TYPE: DNA (genomic)

(iii) HYPOTHETICAL: NO (xi) SEQUENCE DESCRIPTION: SEQ ID NO:4:

CTTCAGCCCA GGGACAACC                                                   19

(2) INFORMATION FOR SEQ ID NO:5:

(i) SEQUENCE CHARACTERISTICS:

```
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:5:

GCAATACGAC TCACTATAG                                              19

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:6:

GGAAGCAGCA GCAAGAACC                                              19

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:7:

CTTCTTTCTC TGCCGCATCG                                             20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:8:

GTGAGGATGA TAGGCCTTCC                                             20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:9:
```

```
CAGAAGCAGA CCAGCAAACC                                                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:10:

CTTCTTTCTC TGCCGCATCG                                                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:11:

CTCTGGAGCA GTGCAATGTG                                                    20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:12:

GTGAGGATGA TAGGCCTTCC                                                    20

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:13:

ATGAATTCCT AATCCTCCTC TGC                                                23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: unknown
        (D) TOPOLOGY: unknown
```

```
        (ii) MOLECULE TYPE: DNA (genomic)

(iii) HYPOTHETICAL: NO (xi) SEQUENCE DESCRIPTION: SEQ ID NO:14:

ATGGATCCAT GAGCGCACGC GGT                                                    23
```